United States Patent
Kimura et al.

(10) Patent No.: US 8,685,710 B2
(45) Date of Patent: Apr. 1, 2014

(54) PHOTODETECTOR AND MEASUREMENT OBJECT READER

(75) Inventors: Kenichi Kimura, Tokyo (JP); Ken Tsukii, Tokyo (JP); Shinichi Taguchi, Tokyo (JP); Jie Xu, Tokyo (JP); Motosuke Kiyohara, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 889 days.

(21) Appl. No.: 12/187,872

(22) Filed: Aug. 7, 2008

(65) Prior Publication Data

US 2009/0032731 A1 Feb. 5, 2009

Related U.S. Application Data

(63) Continuation of application No. PCT/JP2007/005958, filed on Feb. 6, 2007.

(30) Foreign Application Priority Data

Feb. 7, 2006 (JP) ................................. 2006-029239
Apr. 20, 2006 (JP) ................................. 2006-116387

(51) Int. Cl.
*C12M 1/34* (2006.01)
*C12M 3/00* (2006.01)
*G02B 6/00* (2006.01)
*G01N 21/00* (2006.01)
*G01N 21/01* (2006.01)
*G01N 21/64* (2006.01)
*G01N 21/66* (2006.01)

(52) U.S. Cl.
USPC .... 435/287.1; 435/287.2; 385/12; 422/82.05; 422/82.06; 422/82.08; 422/82.11

(58) Field of Classification Search
USPC ............ 435/287.1, 287.2; 385/12; 422/82.05, 422/82.06, 82.08, 82.11; 436/164
See application file for complete search history.

(56) References Cited

U.S. PATENT DOCUMENTS

| 7,154,083 B2 | 12/2006 | Mizuno |
| 2001/0046712 A1* | 11/2001 | Hang et al. ................... 436/172 |
| 2003/0199097 A1 | 10/2003 | Suzuki et al. |
| 2004/0173760 A1* | 9/2004 | Kino et al. ................. 250/458.1 |

FOREIGN PATENT DOCUMENTS

| JP | 2-203255 | 8/1990 |
| JP | 7-270718 | 10/1995 |
| JP | 10-504397 | 4/1998 |
| JP | 10-185782 | 7/1998 |
| JP | 2000-121559 | 4/2000 |
| JP | 2000-509826 | 8/2000 |
| JP | 2000-304688 | 11/2000 |
| JP | 2000-314703 | 11/2000 |
| JP | 2002-148521 | 5/2002 |
| JP | 2003-28798 | 1/2003 |
| JP | 2003-344777 | 12/2003 |
| JP | 2004-258142 | 9/2004 |
| JP | 2004-333333 | 11/2004 |
| JP | 2005-30919 | 2/2005 |
| JP | 2005-230202 | 9/2005 |
| WO | WO 96/09548 | 3/1996 |
| WO | WO 98/38495 | 9/1998 |

OTHER PUBLICATIONS

U.S. Appl. No. 12/403,772, filed Mar. 13, 2009, Tsukii, et al.
Japanese Office Action issued Dec. 26, 2011 in patent application No. 2007-557833 with English translation.

* cited by examiner

*Primary Examiner* — Narayan Bhat
(74) *Attorney, Agent, or Firm* — Oblon, Spivak, McClelland, Maier & Neustadt, L.L.P.

(57) ABSTRACT

A photodetector detects fluorescence emitted from a sample placed on a substrate of a DNA chip. There is an irradiation optical system for guiding irradiation light by a first optical waveguide, gathering the irradiation light by a first lens and irradiating the sample. A reception optical system gathers fluorescence at an input-side end surface of a second optical waveguide by a second lens and guides the fluorescence to a measuring unit. The irradiation optical system and the reception optical system are separate light guiding paths. The reception optical system is of a confocal optical system in which a focal point on the sample is identical to a focal point at the input-side end surface of the second optical waveguide of the reception optical system.

34 Claims, 15 Drawing Sheets

B-B CROSS SECTION

C-C CROSS SECTION

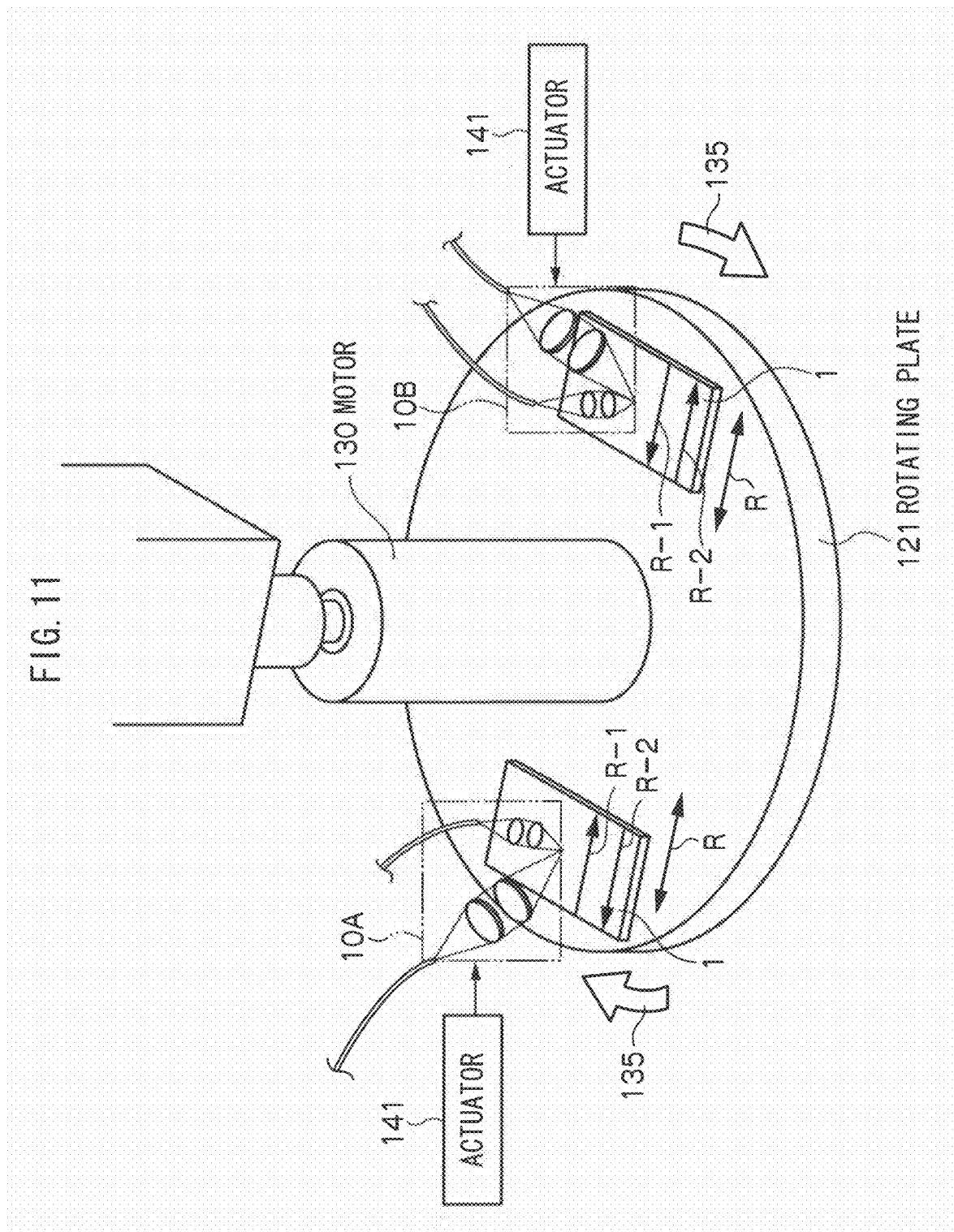

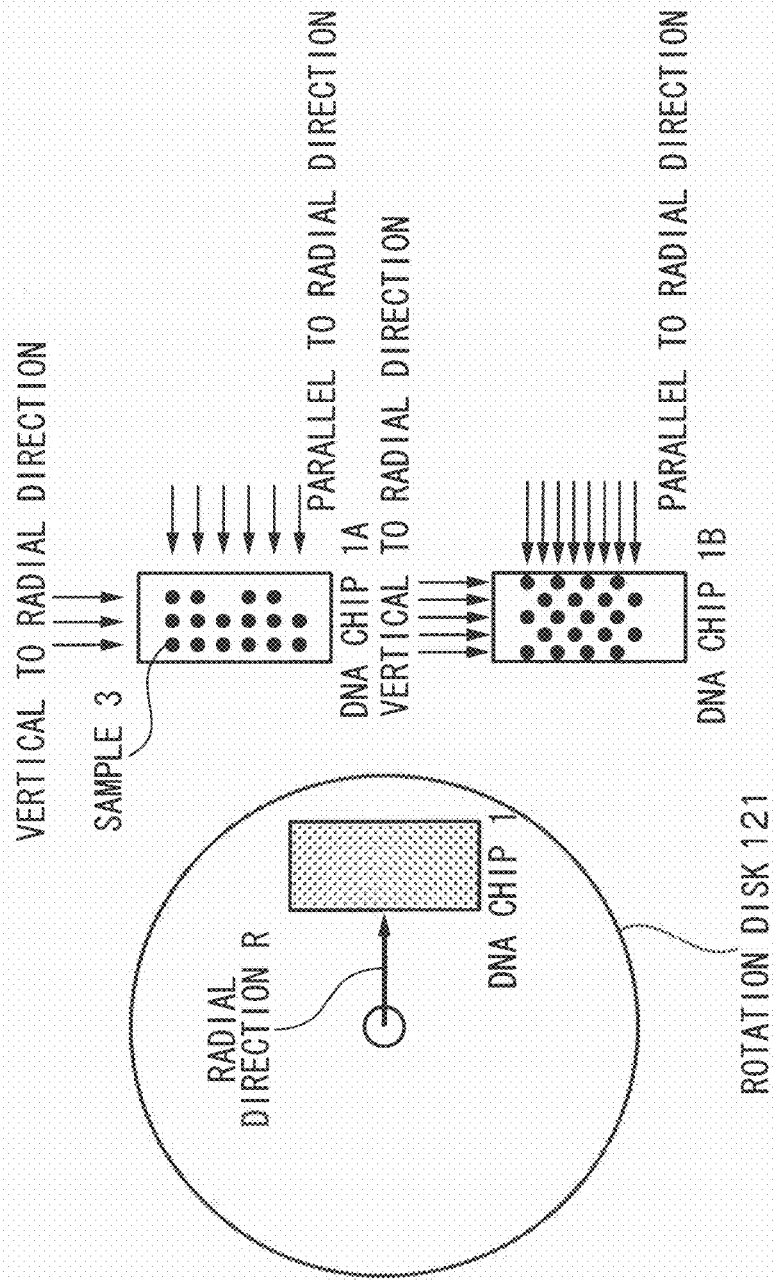

PHOTODETECTOR AND MEASUREMENT OBJECT READER

TECHNICAL FIELD

The present invention relates to a photodetector for reading excitation light (for example, fluorescence) from a sample, and a measurement object reader provided with the optical reader.

BACKGROUND ART

Studies on macromolecules are made for various fields such as clinical examination, drug discovery, and environment or food evaluation, and there are increasing demands for a detector for analyzing information A conventional detector is a device for irradiating a sample on a substrate as a measurement object with light and receiving fluorescence emitted from a fluorescent dye of the sample. For example, there has been proposed a detector structured to irradiate a reaction area of a sample on a board with laser light and detecting light reflected from the reaction area by a photodetecting unit (see patent document 1, for example).

In addition, a conventional substrate measuring unit which uses light has a positionally-fixed optical system, a rotary drive stage and a horizontal drive stage. This optical system is used to irradiate a sample on a substrate as a measurement object with light thereby to detect fluorescence emitted from fluorescent dye of the sample.

The substrate is positioned on the rotary drive stage. When this rotary drive stage is rotated by a motor, the horizontal drive stage moves linearly integral with rotary derive stage and the motor. With this structure, the positionally-fixed optical system and the substrate on the rotary drive stage move relative to each other, the optical system irradiates the sample on the substrate with light and receives light from the sample (see patent document 2, for example).

[Patent document 1] Japanese Patent Application Publication No. 2005-30919
[Patent document 2] Japanese Patent Application Publication No. 2000-304688

DISCLOSURE OF INVENTION

Problems to be Solved by the Invention

However, as the conventional photodetector is structured to simply detect light from a reaction area, it has a problem of detecting reflected light other than fluorescence which is unnecessary for measurement thereby to prevent accurate detection of information of the sample.

In addition, in the conventional substrate measuring unit, as the horizontal drive stage moves together with the rotary drive stage and the motor for rotating the rotary drive stage, that is, it horizontally moves straightly while the rotary drive stage is rotating, the rotary state of the rotary drive stage and the horizontal movement influence each other to cause vibration, which may prevent accurate measurement of the sample on the substrate on the rotary drive stage.

Then, in order to solve the above-mentioned problems, the present invention has an object to provide a photodetector capable of detecting fluorescence emitted from a sample with high accuracy, high sensitivity and high efficiency while avoiding unnecessary reflected light from the sample, and a measurement object reader capable of reading the sample on a substrate as a measurement object at high speed, with high accuracy and high efficiency.

Means for Solving the Problem

In order to solve the above-mentioned problems, a first aspect of the present invention is a photodetector for detecting light emitted from a sample on a substrate as a measurement object, the photodetector comprising: an irradiation optical system for guiding irradiation light by a first optical waveguide, gathering the irradiation light by a first lens and irradiating the sample as the measurement object; and a reception optical system for gathering light emitted from the sample at an input-side end surface of a second optical waveguide by a second lens and guiding the light to a measuring unit, the irradiation optical system and the reception optical system being separate light guiding paths, and the reception optical system being of a confocal optical system in which a focal point on the sample is identical to a focal point at the input-side end surface of the second optical waveguide of the reception optical system.

The photodetector of the present invention is preferably characterized in that in a plane perpendicular to an installation plane on which the measurement object is placed, a first plane including a first optical axis of the irradiation optical system and a second plane including a second optical axis of the reception optical system are not in one plane.

The photodetector of the present invention is preferably characterized in that the irradiation optical system and the reception optical system are inclined any respective angles relative to a plane perpendicular to an installation plane on which the measurement object is placed, so that the irradiation light from the irradiation optical system is mirror-reflected on the substrate as the measurement object and is not received by the reception optical system.

The photodetector of the present invention is preferably characterized in that the axis perpendicular to the installation plane on which the measurement object is placed and the center of the first optical axis of the irradiation optical system form an angle ranging from 10 degrees to 60 degrees, inclusive.

The photodetector of the present invention is preferably characterized in that the axis perpendicular to the installation plane on which the measurement object is placed and the center of the second optical axis of the reception optical system form an angle ranging from 10 degrees to 80 degrees, inclusive.

The photodetector of the present invention is preferably characterized in that a size of a light gathering surface of the irradiation optical system is equal to or less than one fifth of a size of a spot area for measurement.

The photodetector of the present invention is preferably characterized in that a GRIN lens is arranged on an input-side end surface of the irradiation light in the first waveguide of the irradiation optical system.

The photodetector of the present invention is preferably characterized in that a numerical aperture of the second lens of the reception optical system is larger than a numerical aperture of the second optical waveguide.

The photodetector of the present invention is preferably characterized in that a mode field diameter (MFD) of the reception optical system is adjustable.

A measurement object reader of the present invention is a measurement object reader comprising: a measurement object rotating part having a rotator and rotating the rotator with the sample on the substrate as the measurement object placed thereon; the photodetector according to any one of claims 1 to 9 for emitting the irradiation light onto the sample as the measurement object on the rotator thereby to read fluorescence emitted from the sample; and a mechanism for linearly move the photodetector or an irradiation spot toward a center of the rotator or in an opposite direction thereof.

The measurement object reader of the present invention is preferably characterized in that the photodetector comprises a plurality of photodetectors.

The measurement object reader of the present invention is preferably characterized in that the plural photodetectors are arranged in opposite directions about a rotational center of the measurement object rotating part, and the plural photodetectors use light of different wavelengths.

The measurement object reader of the present invention is preferably characterized in that when each of the photodetectors detects the measurement object in a spiral pattern while the rotator is rotated thereby to obtain detection data of the measurement object, the detection data of the measurement object is converted from the spiral pattern into a row-and-column matrix pattern.

The measurement object reader of the present invention is preferably characterized in that a detection sampling speed of the measurement object is increased in measurement of the measurement object at an outer orbit portion of the rotator and decreased in measurement of the measurement object at an inner orbit portion of the rotator, and the speed is changed gradually.

The measurement object reader of the present invention is preferably characterized in that a rotational speed of the rotor is decreased in measurement of the measurement object at an outer orbit portion of the rotator and increased in measurement of the measurement object at an inner orbit portion of the rotator, and the speed is changed gradually.

The measurement object reader of the present invention is preferably characterized in that the detection data of the sample is obtained plural times by changing a focal point distance of the light in the irradiation optical system.

The measurement object reader of the present invention is preferably characterized in that the rotator is a circular disk and a plurality of chips of similar or different kinds is detachably fixed onto the round disk thereby to measure the plurality of chips.

The measurement object reader of the present invention is preferably characterized in that the plurality of chips is analyzed simultaneously.

The measurement object reader of the present invention is preferably characterized in that analysis results of the plurality of chips are analyzed comprehensively.

The measurement object reader of the present invention is preferably characterized in that some of the plurality of chips are different in pretreatment method.

The measurement object reader of the present invention is preferably characterized in that the plurality of chips includes a gene expression analysis chip and a genomic analysis chip.

The photodetector of the present invention is preferably characterized in that the axis perpendicular to the installation plane on which the measurement object is placed and the center of the first optical axis of the irradiation optical system are arranged forming any angle while a spot shape to the measurement object is a circle.

The photodetector of the present invention is preferably characterized in that a noncircular ratio of the spot shape is equal to or less than 20%.

The photodetector of the present invention is preferably characterized in that a cylindrical lens is used to form a circular spot.

The measurement object reader of the present invention is preferably characterized in that the plural photodetectors moves linearly toward the center of the rotator or in an opposite direction thereof, and the plural photodetectors reciprocate toward the center of the rotator or in the opposite direction thereof thereby to perform detection.

The measurement object reader of the present invention is preferably characterized in that in reciprocating, the photodetectors move at different speeds between a return path and a return path.

The measurement object reader of the present invention is preferably characterized in that there are an orbit at which each of the photodetectors conduct measurement and an orbit at which the photodetector does not conduct measurement while the rotator rotates, in the orbit at which the photodetector does not conduct measurement, measured data of a chip is transferred from a memory to an analyzer, and the measured data is analyzed by a next orbit at which the photodetector does not conduct measurement.

The measurement object reader of the present invention is preferably characterized in that wherein chips to be analyzed are single or plural.

The measurement object reader of the present invention is preferably characterized in that as the irradiation optical system gathers a focal point of the light on each of the chips, an upper surface of the chip is used as a reference.

A measurement object reader of the present invention is a measurement object reader having a photodetector for detecting light emitted from a sample on a substrate as a measurement object, the measurement object reader comprising: an irradiation optical system for guiding irradiation light by a first optical waveguide, gathering the irradiation light by a first lens and irradiating the sample as the measurement object; a reception optical system for gathering light emitted from the sample at an input-side end surface of a second optical waveguide by a second lens and guiding the light to a measuring unit, the reception optical system being a light guiding path separate from a light guiding path of the irradiation optical system and, and the reception optical system being of a confocal optical system in which a focal point on the sample is identical to a focal point at the input-side end surface of the second optical waveguide of the reception optical system; a measurement object rotating part having a rotator and rotating the rotator with the sample on the substrate as the measurement object placed thereon; the photodetector for emitting the irradiation light onto the sample as the measurement object on the rotator thereby to read fluorescence emitted from the sample; and a mechanism for linearly move the photodetector or an irradiation spot toward a center of the rotator or in an opposite direction thereof.

The measurement object reader of the present invention is preferably characterized in that the irradiation optical system and the reception optical system move together while maintaining their relative positions of the confocal optical system.

The measurement object reader of the present invention is preferably characterized in that each of the chips has samples of which rows and columns are arranged in parallel with or vertical to a radial direction of the rotator.

The measurement object reader of the present invention is preferably characterized in that in each of the chips, a plane where the samples are placed is shaped like a rectangle or a square.

Effects of the Invention

According to the optical reader according to the present invention, it is possible to read excitation light such as fluorescence from a sample with high accuracy, sensitivity and efficiency, while avoiding unnecessary reflected light from the sample.

BRIEF DESCRIPTION OF DRAWINGS

FIG. 11 is a view showing reciprocating movement of plural photodetectors relative to the respective DNA chips;

FIG. 16 is a view showing samples arranged in rows and columns in parallel with or vertical to the radial direction of the rotator.

BRIEF DESCRIPTION OF REFERENCES

Figure 1:
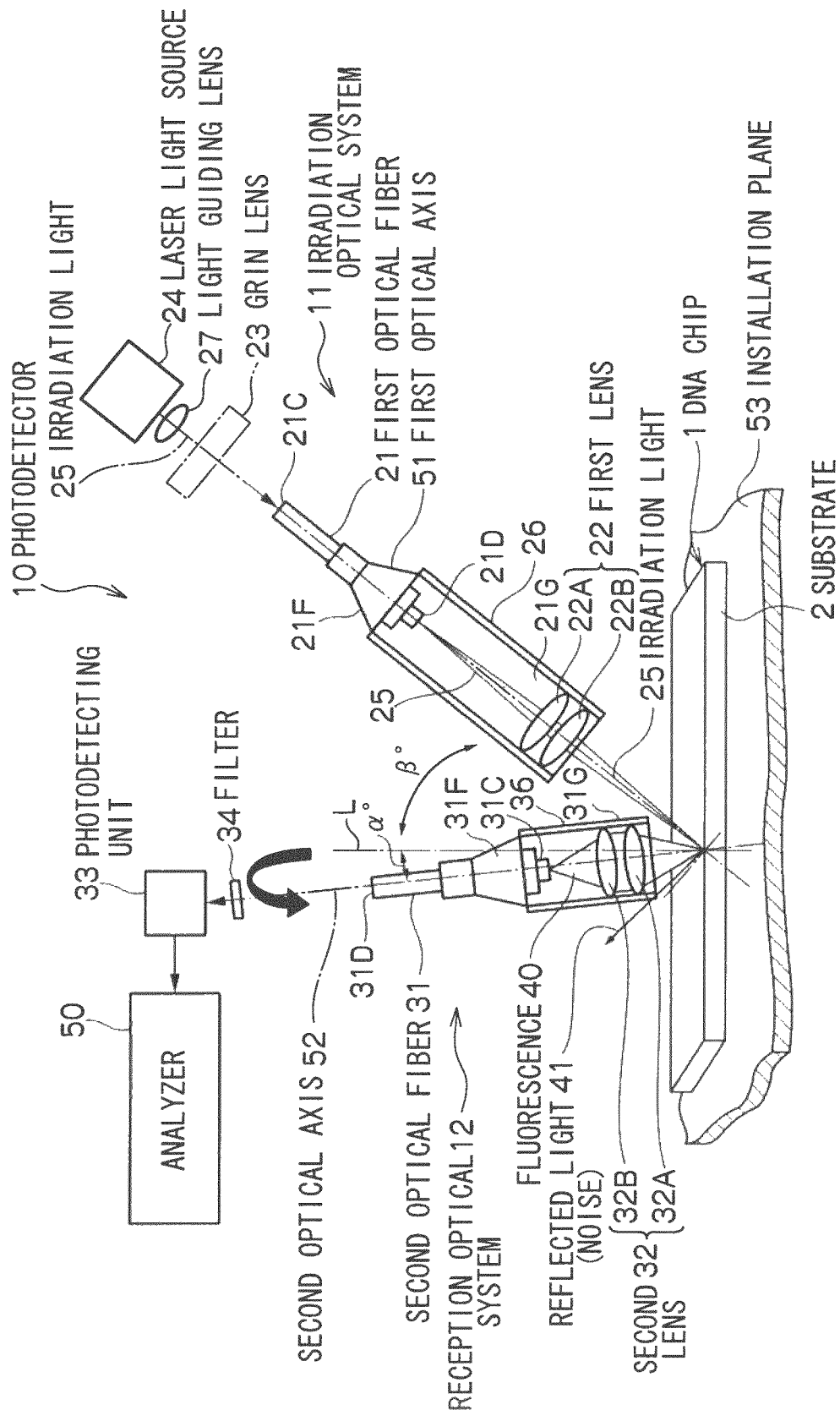
FIG. 1 is a perspective view illustrating a structure of a photodetector according to a preferred embodiment of the present invention.

1 . . . DNA chip (one example of a measurement object)
1A . . . chip (one example of a measurement object)
1B . . . chip (one example of a measurement object)
2 . . . substrate
3 . . . sample
10 . . . photodetector
11 . . . irradiation optical system
12 . . . reception optical system
21 . . . first optical fiber (first optical waveguide)
22 . . . first lens
23 . . . GRIN lens
24 . . . laser light source
25 . . . irradiation light
26 . . . tube member
27 . . . light guiding lens
31 . . . second optical fiber (second optical waveguide)
32 . . . second lens
33 . . . photodetector (one example of measurement unit)
34 . . . filter
40 . . . fluorescence radiated from a sample
41 . . . reflected light (noise)
51 . . . first optical axis
52 . . . second optical axis
100 . . . measurement object reader
120 . . . measurement object rotating part
130 . . . driving part
141 . . . first actuator
142 . . . second actuator

BEST MODES FOR CARRYING OUT THE INVENTION

With reference to the drawings, a photodetector according to a preferred embodiment of the present invention will now be described below.

Figure 2:
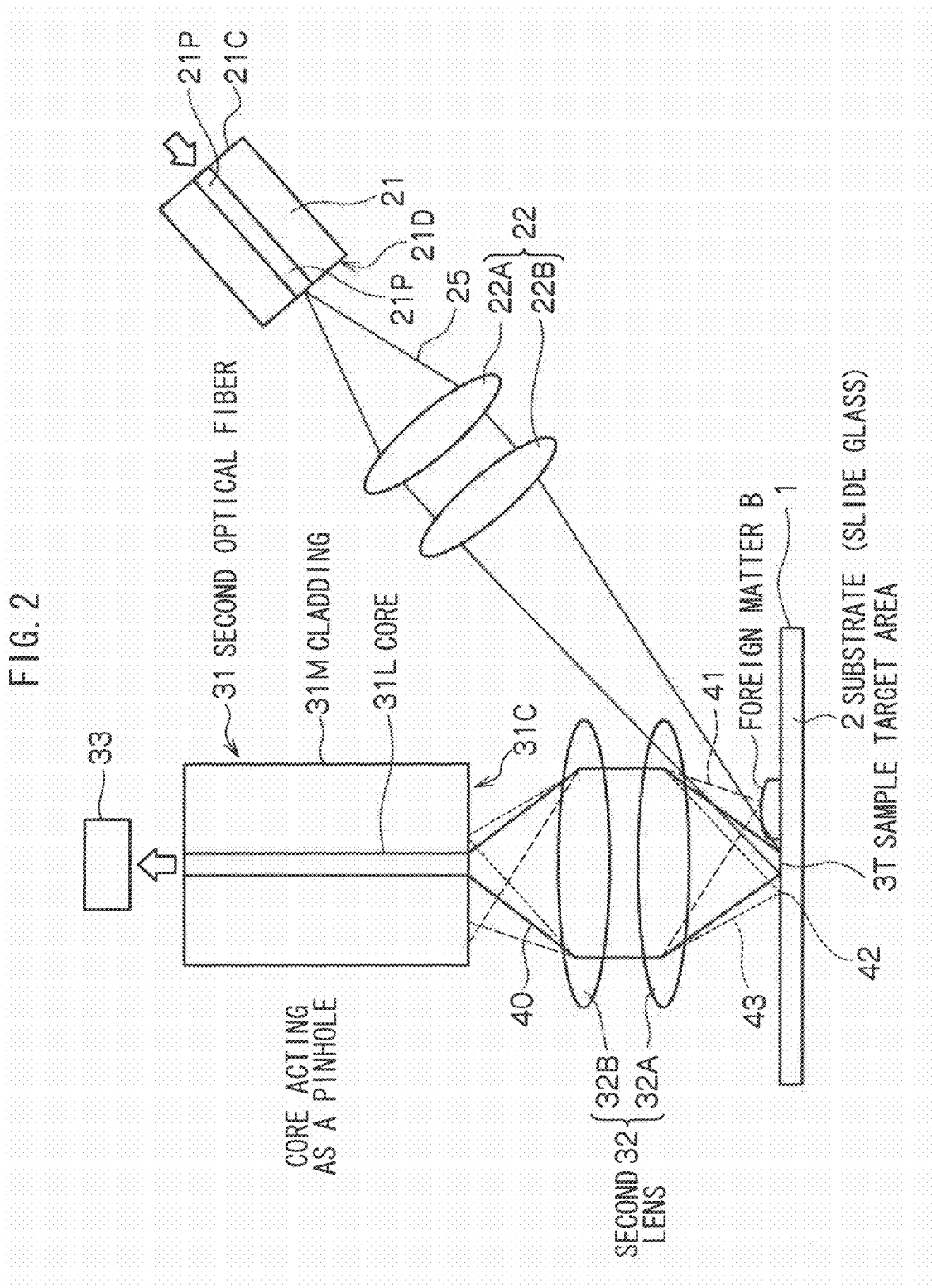
FIG. 2 is a view of a structural example of a confocal reception optical system, illustrating more details of the optical system of the photodetector of FIG. 1.

FIG. 1 is a view illustrating a structure of a photodetector according to the preferred embodiment of the present invention. FIG. 2 is a view specifically illustrating optical system elements of the photodetector of FIG. 1.

As shown in FIG. 1, the photodetector 10 is an apparatus for optically reading light such as fluorescence emitted from a measurement object, for example, a sample arranged on a substrate 2 of a DNA chip 1.

The photodetector of FIG. 1 has an irradiation optical system 11 and a reception optical system 12, which are separate light guiding paths.

The irradiation optical system 11 has a first optical fiber 21 as a first optical waveguide, a first lens 22, a GRIN lens 23, a laser light source 24 and a light guiding lens 27. The first optical fiber 21 has an input-side end surface 21C and an output-side end surface 21D.

The laser light source 24 in FIG. 1 emits, for example, green laser light having a wavelength of 532 nm or red laser light having a wavelength of 635 nm as irradiation light 25. The irradiation light 25 from the laser light source 24 passes through the light guiding lens 27 and the GRIN lens 23 and is inserted into the core 21P of the input-side end surface 21C of the first optical fiber 21. The GRIN lens 23 is a tube-line lens having a refractive index gradually inclined in a radial pattern. Usually, the input conditions (spot diameter and irradiation angle) of the first optical fiber 21 are restrained by inherent to numerical aperture and core diameter inherent to the first optical fiber 21. However, as the GRIN lens 23 is used before the first optical fiber 21, the input conditions are restrained by the GRIN lens 23. For this reason, if the irradiation light 25 can be inserted into the GRIN lens 23, the irradiation light 25 can be inserted into the first optical fiber, even when the core diameter of the first optical fiber 21 is too small to receive the irradiation light 25. Therefore, the irradiation light 25 can be surely inserted into the core 21P of the input-side end surface 21C of the first optical fiber 21.

The first optical fiber 21 in FIG. 1 has a holder 21F, which has a tube member 26 at the output-side end surface of the first optical fiber 21. The tube member 26 has an end fixed to the holder 21F and another end which is an opening 21G.

At the opening 21G of the tube member 26, there is a first lens 22, which has two lens members 22A and 22B. These lens members 22A and 22B are used to collimate irradiation light 25 emitted from the output-side end surface 21D of the first optical fiber 21 and focus the light to have a given irradiation diameter. The irradiation light focused to have the given irradiation diameter is emitted onto the sample 2 on the DNA chip shown in FIG. 2.

Next, the reception optical system 12 has a second optical fiber 31 as second optical waveguide, second lens 32, a photodetecting unit 33 and a filter 34.

The photodetecting unit 33 used here may be a photomultiplier (photoelectron multiplier). As the photo-multiplier is used as the photodetecting unit 33, fluorescence 40 can be surely received with high precision and subjected to optoelectronic conversion.

The second optical fiber 31 for photodetection in FIG. 1 has an input-side end surface 31C and an output-side end surface 31D of the fluorescence 40. The second optical fiber 31 has a holder 31F, which has a tube member 36 at the input-side end surface 31C side of the second optical fiber 31. The tube member 36 has an end fixed to the holder 31F and another end which is an opening 31G.

At the opening 31G of the tube member 36, there is a second lens 32, which has two lens members 32A and 32B. These lens members 32A and 32B are used to collimate fluorescence 40 emitted from the fluorescent dye of the sample and focus the fluorescence to have a focal point at the core 31L of the input-side end surface 31C of the second optical fiber 31.

The tube member 26 as shown in FIG. 1 acts to cut off light so as to prevent inserting of disturbance light into the input-side end surface 21C of the first optical fiber 21 and the first lens 22, and also connects the first lens 22 to the holder 21F mechanically. The tube member 36 acts to cut off light so as to prevent inserting of disturbance light into the input-side end surface 31C of the second optical fiber 31 and the second lens 32, and also connects the second lens 32 and the holder 31F mechanically.

FIG. 2 shows a structural example of the confocal-type reception optical system 12.

FIG. 2 shows the above-described first lens 22, first optical fiber 21, second lens 32, second optical fiber 31 and DNA chip 1. However, the holder 21F, tube member 26, holder 31F and tube member 36 are omitted from the view for simplification.

As shown in FIG. 2, when the irradiation light shown in FIG. 1 is radiated to the sample and fluorescence 40 is emitted from the fluorescent dye at the target area 3T of the sample, the fluorescence 40 passes through the second lens 32 and comes into a focal point on the core 31L of the second optical fiber 31 at the input-side end surface 31C of the second optical fiber 31.

The second optical fiber 31 is structured having the core 31L, cladding 31M around the core 31L and a coating (not shown) coating the cladding 31M.

Guiding of the fluorescence 40 into the second optical fiber 31 is performed with use of this core 31L, and the core 31L acts as a pinhole even if there is provided no separate optical member having a pinhole usually used in a reception optical system of the confocal system. In other words, the core 31L of the input-side end surface 31C of the second optical fiber 31 of the reception optical system 12 acts as a hole, and the same focal point is achieved via the second lens 32 on the target area 3T and the core 31L. As the reflected light 41, 43 as noise shown in FIG. 2 is not input to the core 31L, it is possible to cut off the noise light from a part other than the focal point thereby realizing high sensitivity in detecting of the fluorescence 40.

As shown in FIG. 2, even if there exists a foreign matter B near the target area 3T on the DNA chip 1, the core 31L of the input-side end surface 31C of the second optical fiber 31 is not affected by the reflected right from the foreign matter B. The reason why the core 31L is not affected by the reflected light from this foreign matter B is, as indicated by the broken line in FIG. 2, the reflected light 41 from the foreign matter B is input to the cladding 31M not the core 31L after passing through the second lens 32.

In addition, the reflected light 43 from a part 42 of the substrate 2 other than the target area 3T passes through the second lens 32 and is input to the cladding 31M, not to the core 31L. Therefore, this reflected light 43 does not affect the core 31L at the input-side end surface 31C of the second optical fiber 31.

In this way, the core 31L at the input-side end surface 31C of the second optical fiber 31 can guide only fluorescence 40 emitted from the target area 3T of the DNA chip 1 into the photodetecting unit 33 shown in FIG. 1.

The analyzer 50 shown in FIG. 1 is, for example, a computer, which analyzes the sample of the DNA chip 1 based on fluorescence information from the photodetecting unit 33.

As shown in FIG. 1, the above-described irradiation optical system 11 and the reception optical system 12 are separate light guiding paths. Next description is made about a positional relation between a first optical axis 51 of this irradiation optical system 11 and a second optical axis 52 of the reception optical system 12, and the installation plane 53 of the DNA chip 1.

The irradiation light 25 from the irradiation optical system 11 sometimes causes reflected light 41 from the surface of the DNA chip 1, for example. When the reception optical system 12 receives this reflected light 41, the light 41 becomes noise to reduce the sensitivity. In order to prevent this situation, the irradiation optical system 11 and the reception optical system 12 are provided as separate guiding paths and inclined $\beta$, $\alpha$ respectively relative to the axis L vertical to the installation plane 53.

The DNA chip 1 shown in FIG. 1 is placed on the installation plane 53. In a plane vertical to the installation plane 53, a first plane including the first optical axis 51 of the irradiation optical system 11 and a second plane including the second optical axis 52 of the reception optical system 12 are not the same plane.

Figure 6:
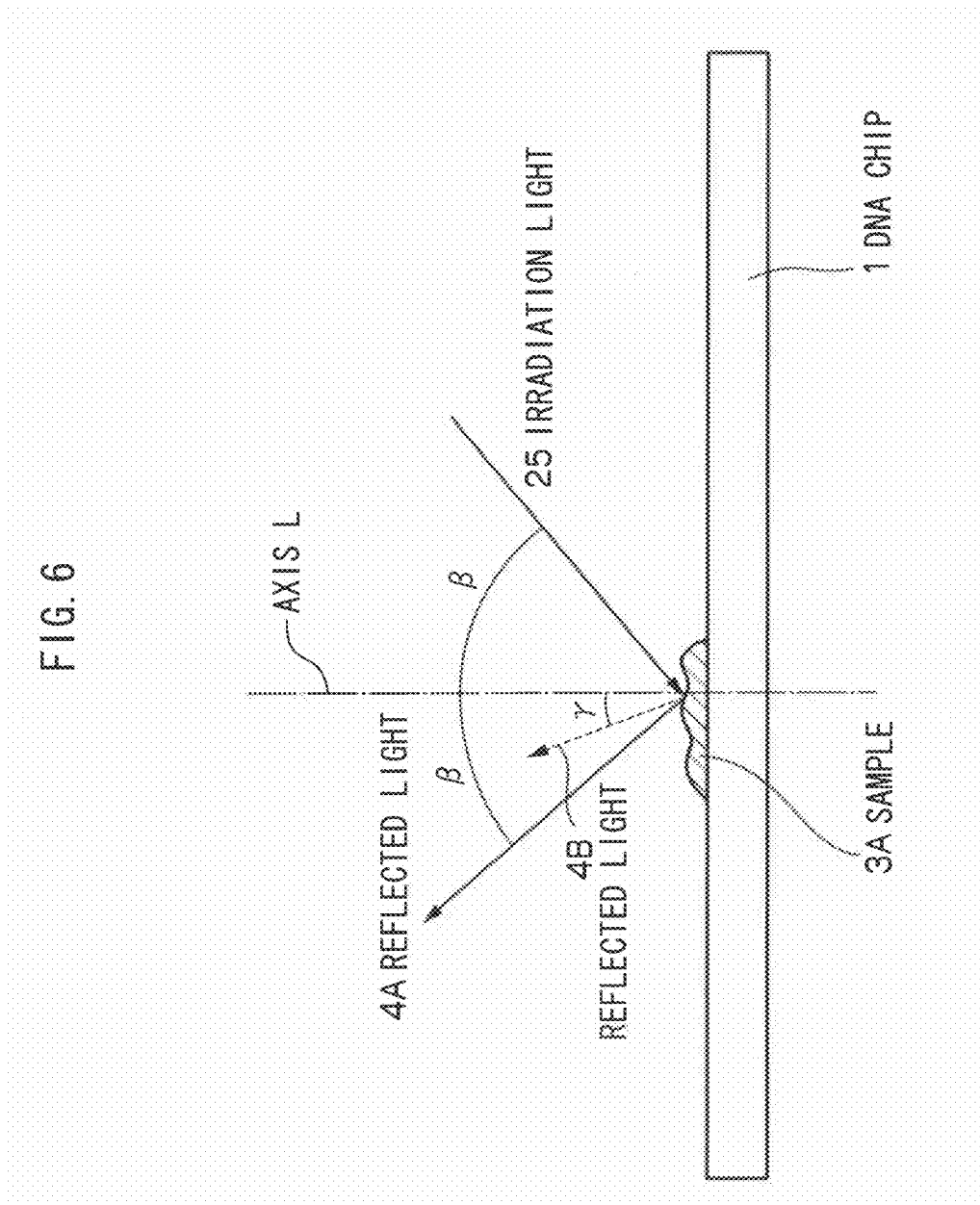
FIG. 6 is a view schematically showing a relation between irradiation light and reflected right.

As shown in FIGS. 1 and 6, the first optical axis 51 of the irradiation optical system 11 is inclined by the angle $\beta$ relative to the axis L vertical to the installation plane 53. The reflected light 41 of the irradiation light 25 passing through the first optical axis 51 includes reflected light beams 4A symmetrically inclined by the angle $\beta$ relative to the axis L and a reflected light beam 4B inclined for example by an angle $\gamma$ depending on a state of the surface of the sample 3A. However, as these reflected light beams 4A and 4B pass through the irradiation optical system 11 and in the first plane vertical to the installation plane 53, the reception optical system 12 is placed in the second plane not in the same as the first plane, which makes it possible to receive a light signal in accordance with its characteristics while preventing adverse affection of noise due to excitation light or the like.

The angle $\beta$ formed by the axis L vertical to the installation plane 53 and the first optical axis 51 of the irradiation optical system 11 preferably ranges from 10 degrees to 60 degrees, inclusive. The angle $\alpha$ formed by the axis L vertical to the installation plane 53 and the second optical axis 52 of the reception optical system 12 preferably ranges from 10 degrees to 80 degrees, inclusive. For example, in the example of FIG. 1, the angle $\alpha$ is 37 degrees and the angle $\beta$ is 39 degrees.

When the angle $\beta$ formed by the axis L vertical to the installation plane 53 and the first optical axis 51 of the irradiation optical system 11 is set to 0 or around 0, for example, reflected light is emitted to the tube member 26 of the irradiation optical system 11 and then, there occurs diffuse reflection around the tube member 26. This may affect as noise on the performance, which results in degradation of the sensitivity. In order to prevent this affect, the angle $\beta$ is preferably 10 degrees or more.

Figure 14:
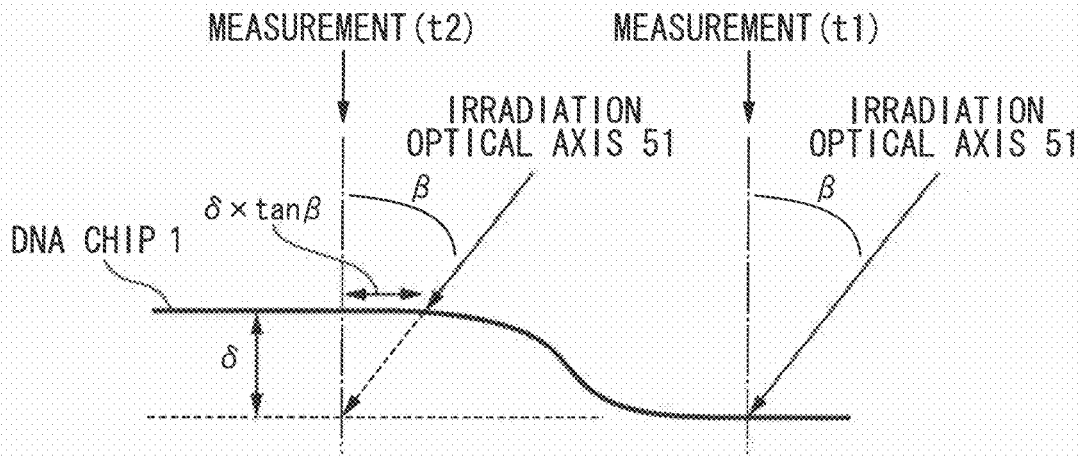
FIG. 14 is view showing a measurement example when there is an elevation change in the DNA chip.

In addition, as the angle $\beta$ is provided between the installation plane 53 and the first optical axis 51 of the irradiation optical system 11, for example, when there is an elevation change at the DNA chip 1 as shown in FIG. 14, there occurs fluctuation ∂ in positional relationship between the irradiation optical system 11 and the DNA chip 1 in the direction of the axis L vertical to the installation plane 53, and then, the spot center of light emitted to the DNA chip 1 by the irradiation optical system 11 is shifted from a target position, which causes reduction in resolution. The shift of the spot center is expressed by ∂×tan β and increases in proportion to tan β. If the angle β becomes too large, affection by the positional fluctuation ∂ a becomes larger undesirably. Particularly, if the angle β exceeds 60 degrees, tan β becomes about 2, which influence is not negligible. Therefore, the angle β is preferably 60 degrees or less.

Figure 15:
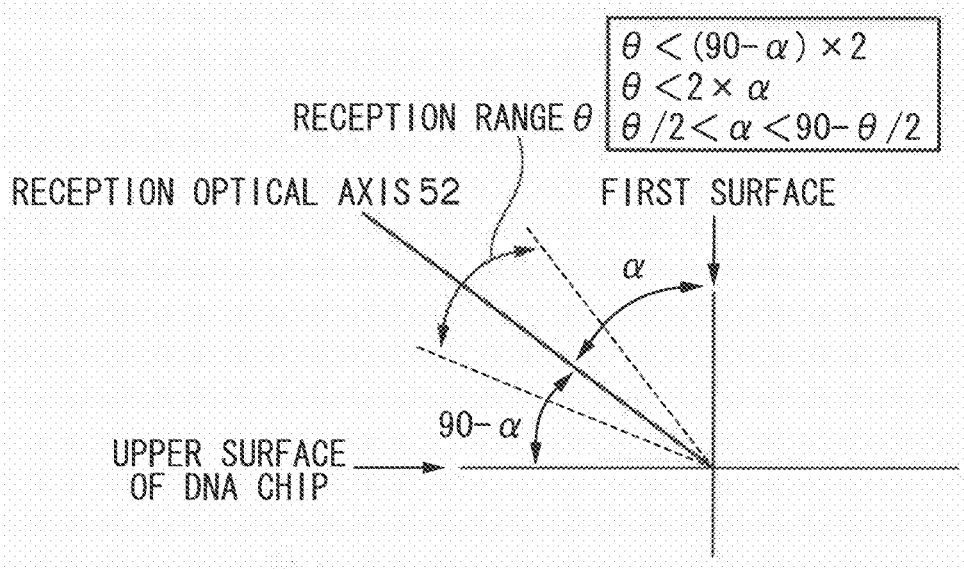
FIG. 15 is a view showing light receiving area of an angle θ around the second optical axis in accordance with the numerical apertures of the second optical fiber and the second lens.

As shown in FIG. 6, for example, the light emitted from the irradiation optical system 11 is reflected as reflected light 4B at the angle γ by the sample 3A on the DNA chip 1. As this reflected light is emitted symmetrically with the first optical axis 51 of the irradiation optical system 11 with respect to the vertical line to the irradiation surface of the sample 3A, the area of light emission in the first plane including the first optical axis 51 of the irradiation optical system 11 may vary with shapes of the sample 3A. Therefore, when a fluorescence signal in the first plane including the first optical axis 51 of the irradiation optical system 11 is received, reflected light as noise may be also received with the fluorescence signal undesirably. With this structure, as shown in FIG. 15, the reception optical system 12 is capable of receive light in an area of the angle β with respect to the second optical axis 52 according to the numerical apertures of the second optical fiber 31 and the second lens 32. In order to enhance the sensitivity, the reception area is preferably wide, however, the reception area preferably does not include the first plane including the first optical axis 51 of the irradiation light 11. To meet this requirement, it is necessary to make the axis L vertical to the installation plane 53 and the second optical axis 52 of the reception optical system 12 form the angle α and not to include the reception area θ in the first plane including the first optical axis 51 of the irradiation optical system 11. As the reception area θ is limited to less than 2×α, the angle α is preferably 10 degrees or more so as to ensure the minimal reception area.

However, as shown in FIG. 15, the reception area θ angle is structurally limited to less than (90−α)×2 degrees so as not to contact with the DNA chip 1 as the measurement object, and on the other hand, the angle α formed with the second optical axis 52 of the reception optical system 12 becomes too large, which undesirably leads to reduction in sensitivity. In fact, for example, as the second lens 32 and the tube member 32 supporting the second lens 32 in FIG. 1 are also required not to be in contact with the DNA chip 1, further restriction to the angle is required. In order to assure enough reception area β, the angle α is preferably 60 degrees or less.

The size of converging surface (irradiation diameter) in the target area 3T of the irradiation light 25 from the irradiation optical system 11 as shown in FIGS. 1 and 2 needs to be one fifth of one spot area of the sample 3 in the DNA chip 1 so as to achieve enough resolution. More preferably, the irradiation diameter is equal to or less than a predetermined resolution. In the embodiment of FIG. 1, the irradiation diameter is, for example, 5 μm. For example, when one spot area of the sample 3 is 100 μm, the irradiation diameter is preferably one twentieth or less, and when the irradiation diameter is 20 μm or larger, enough resolution is disadvantageously hard to obtain for its spot diameter. Besides, if the predetermined resolution is 5 μm, for example, and the irradiation diameter is more than 5 μm, the fluorescence information is received from the outside of the measurement area as noise. Therefore, the irradiation diameter is preferably 5 μm or less.

Preferably, the MFD (Mode Field Diameter) of the first optical fiber 21 of the irradiation optical system is equal to or less than three times of the size of converging surface (irradiation diameter) in the target area of the irradiation light 25. The MFD is a diameter of a light propagating area including a part of the cladding 31M and the core 31L of the first optical fiber 21 through which the irradiation light 25 passes. When the MFD is larger than a target irradiation diameter, it is necessary to change the image magnification so as to realize the target irradiation diameter, which requires to change a distance from the output-side end surface 21D of the first optical fiber 21 and the first lens 22A with respect to the distance from the first lens 22B to the target area 3T according to the image magnification. For example, if the MFD is twice the target irradiation diameter and the distance from the first lens 22B to the target area 3T is fixed, the distance from the output-side end surface 21D of the first optical fiber 21 to the first lens 22A needs to be twice. The longer the optical path is, the larger aberration tends to be. Hence, the MFD is preferably equal to or less than three times the target irradiation diameter. If the MFD becomes larger than three times the target irradiation diameter, the aberration becomes extremely large undesirably.

As the GRIN lens 23 is arranged to the input-side end surface 21C side of the first optical fiber 21 of the irradiation optical system 11 in FIG. 1, it is possible to enhance the input efficiency of the irradiation light 25 from the laser light source 24 into the input-side end surface 21C side of the first optical fiber 21.

The larger the numerical apertures pf the second optical fiber 31 and the second lens 32 of the reception optical system 12, the better the performance is, and light receiving angle of the fluorescence 40 is broadened thereby allowing highly-sensitive measurement. If the numerical aperture of the second lens 32 of the reception optical system is greater than or equal to that of the second optical fiber 31, preferably it becomes possible to make the most effective use of the numerical aperture of the optical fiber 31. More preferably, the numerical apertures of the second optical fiber 31 and the second lens 32 are 0.3 or more, thereby enabling reliable photodetection of the fluorescence 40. Or, for example, if the second optical fiber 31 is exchanged into another king of fiber and the mode field diameter (MFD) of the second optical fiber 31 of the reception optical system 12 is changed, it becomes possible to allow flexible change the photodetecting sensitivity and focal depth of the fluorescence 40.

Figure 3:
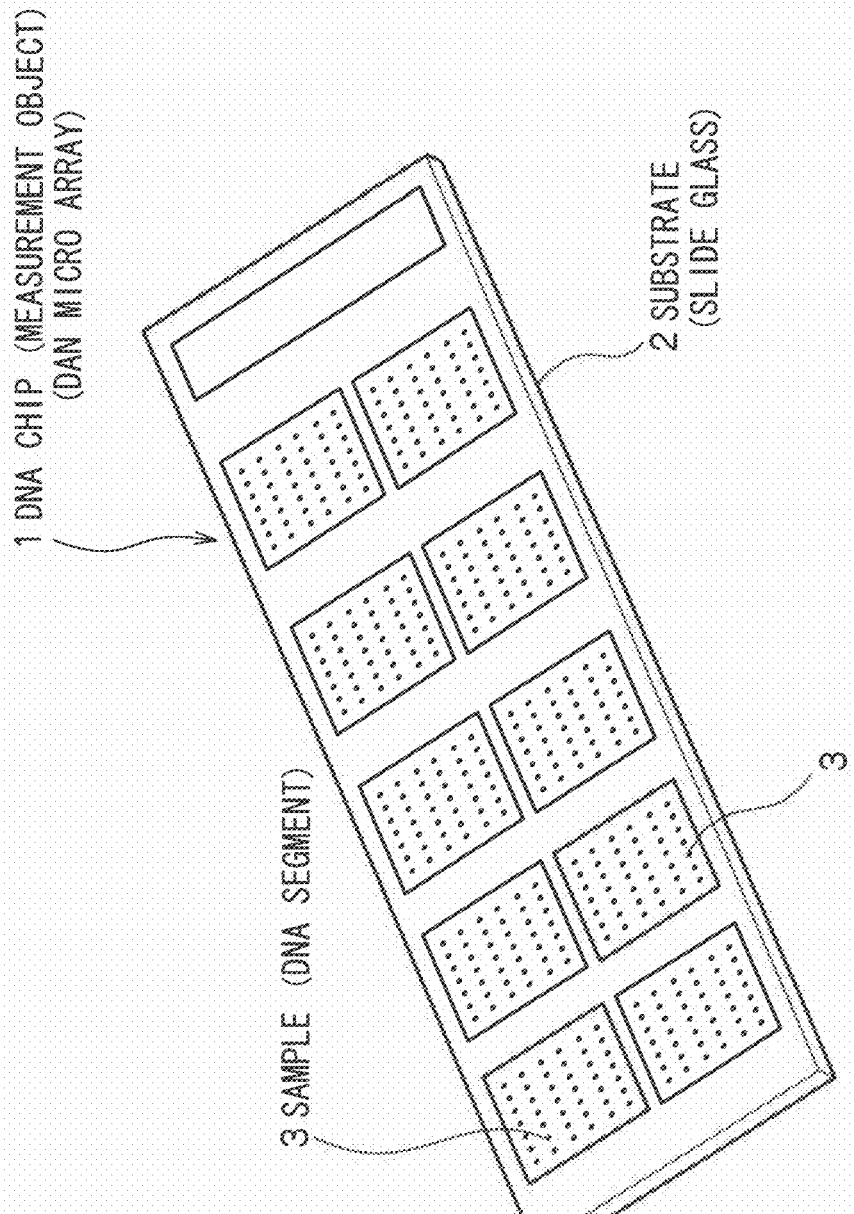
FIG. 3 is a perspective view illustrating a DNA chip as measurement object.

Here, with reference to FIG. 3, description is made about a DNA chip 1 as a measurement object.

The DNA chip 1 is also called NDA micro array in which a plurality of samples 3 is fixed on a substrate such as a slide glass. In this example, each sample 3 is a DNA segment and labeled with fluorescent dye. This DNA chip 1 includes an afimetrics type manufactured with use of semiconductor techniques and a Stanford type having a pin spot.

Next description is made about a photodetecting method of a light including fluorescence of a sample by the above-described photodetector 10.

As shown in FIG. 1, a DNA chip 1 is placed on the installation plane 53. The laser light source 24 emits irradiation light 25 into the input-side end surface 21C of the first optical fiber 21. The irradiation light 25 is guided by the first optical fiber 21 to be emitted from the output-side end surface 21D, has its focal point narrowed by the first lens 22 and is outputted to the target area 3T shown in FIG. 2. The irradiation light 25 excites fluorescence at the target area 3T of the sample 3.

The fluorescence 40 emitted from the sample 3 has its focal point narrowed by the second lens 22 of the reception optical system 12 and is input to the core 31L by the confocal system. Then, the target area 3T and the core 31L have the same focal point via the second lens 32. The reflected light 41, 43 as noise shown in FIG. 2 is not input to the core 31L, and in other words, noise from areas other than the focal point can be cut thereby to allow high sensitivity in detecting of the fluorescence 40.

The input fluorescence 40 passes through the second optical fiber to be detected by the photodetecting unit 33, and then, an analyzer 50 analyzes the sample based on fluorescence from the sample.

In this way, in the above-described photodetector 10, the irradiation optical system 11 is structured to guide the light by the first optical waveguide, focus the light by the first lens 22 and irradiate the measurement object with the light. The reception optical system 12 is structured to focus the fluorescence emitted from the sample by the second lens 32 on the end surface of the second optical waveguide to guide the fluorescence to the measuring unit. The end surface of the second optical waveguide of the reception optical system 12 acts as a pinhole of the confocal optical system. The photodetector 10 is capable of reading fluorescence or the like emitted from the sample with high precision and high sensitivity while avoiding unnecessary reflected light from the sample.

Figure 4:
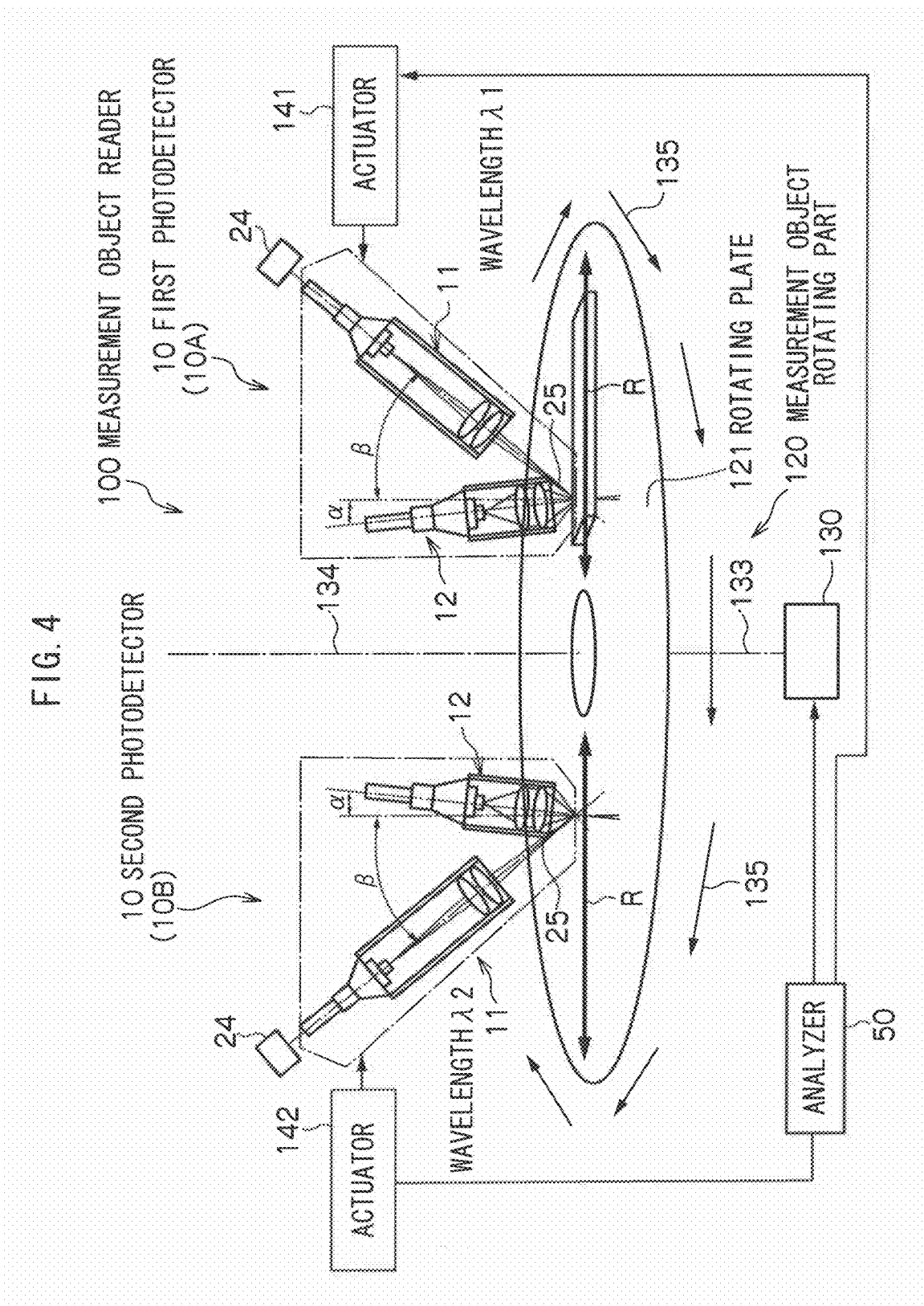
FIG. 4 is a perspective view illustrating an example of measurement object reader equipped with a photodetector according to a preferred embodiment of the present invention.
Figure 5:
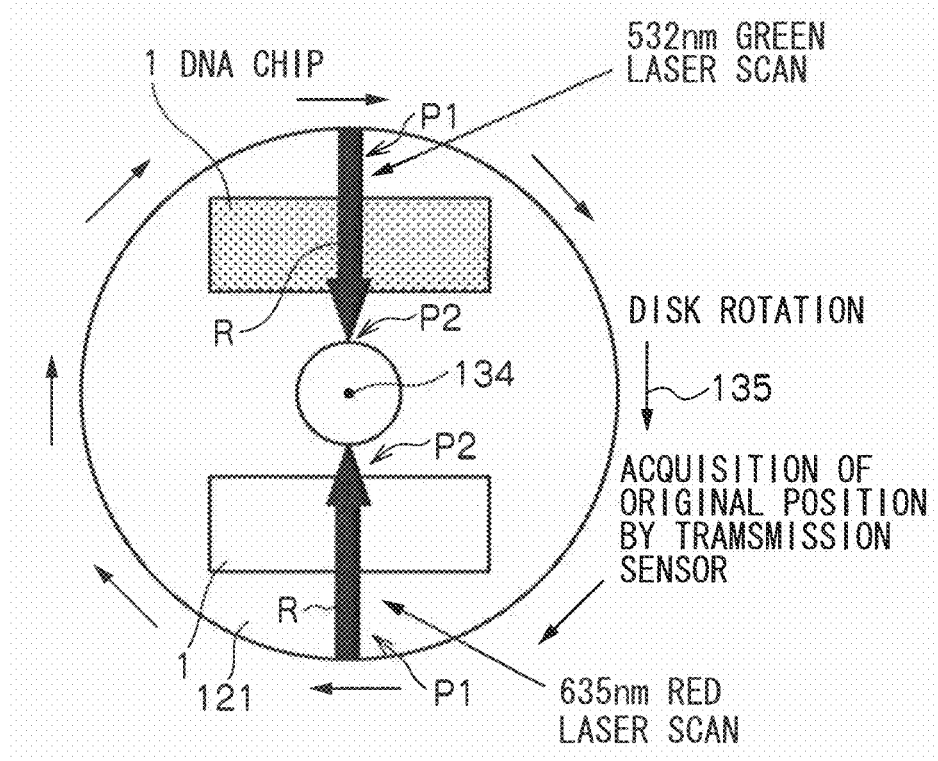
FIG. 5 is a plane view illustrating an arrangement example of samples and a rotator of the measurement object reader according to the preferred embodiment of FIG. 4.

Next description is made about a measurement object reader to which the above-described photodetector 10 is applied, with reference to FIGS. 4 and 5.

The measurement object reader 100 shown in FIG. 4 has two photodetectors 10 as a preferred example. The two photodetectors 10 are a first photodetector 10A and a second photodetector 10B, which have the same structures as the above-described photodetector 10 and description of the photodetector 10 is used for description of these photodetectors 10A and 10B.

The measurement object reader 100 of FIG. 4 has the first photodetector 10A, the second photodetector 10B and a measurement object rotating part 120.

The measurement object rotating part 120 has a rotating plate 121 as a rotation body (disk) and a driving part 130 such as an electric motor. Drive control of the driving part 130 is for example performed on a command signal from analyzer 50 shown in FIG. 1. The measurement object rotating part 120 rotates the rotating plate 121 while a plurality of DNA chips 1 as measurement objects is fixed on the rotating plate 121. The output shaft 133 of the driving part 130 is connected to the center of the rotating plate 121. The rotating plate 121 is capable of rotate continuously, for example, in a direction indicated b the arrow 135 about the rotation center axis 134 of the output shaft 133.

The first photodetector 10A is capable of reciprocating motion along the radial direction R of the rotating plate 121 by the operation of a first actuator 141, while the second photodetector 10B is capable of reciprocating motion along the radial direction R of the rotating plate 121 by the operation of a second actuator 142.

The first actuator 141 has, for example, a guiding part for guiding the first photodetector 10A mechanically and linearly along the radial direction R and a linear motor for moving the first photodetector 10A along the guiding part. Likewise, the second actuator 142 has, for example, a guiding part for guiding the second photodetector 10B mechanically and linearly along the radial direction R and a linear motor for moving the second photodetector 10B along the guiding part.

Besides, the photodetector 10A and the photodetector 10B are arranged in the opposite directions with respect to the center near the rotation center axis 134. The photodetector 10A and the photodetector 10B move (scan) toward the rotation center axis 134 in synchronization with each other, by operation of the first actuator 141 and the second actuator 142, respectively, and move (scan) in the respective directions departing from the rotation center axis 134. During movement, the photodetector 10A and the photodetector 10B keep relative positions in the confocal optical system of their irradiation optical systems 11 and reception optical systems 12.

The laser light source 24 of the first photodetector 10A and the laser light source 24 of the second photodetector 10B shown in FIG. 4 emit irradiation light 25 of different wavelengths. For example, the laser light source 24 of the first photodetector 10A emits green laer light having a wavelength of 532 nm while the laser light source 24 of the second photodetector 10B emits read laser light having a wavelength of 635 nm.

Next description is made about a sample reading method of a measurement object using the measurement object reader 100 equipped with the photodetector 10.

On the rotating plate 121 shown in FIGS. 4 and 5, there is placed a plurality of DNA chips 1. In setting of the DNA chips 1, the longitudinal direction of each of the DNA chips 1 is arranged along the circumferential direction of the rotating plate 121, for example. In FIG. 5, for simplification of the figure, two DNA chips 1 are only shown as an example. Before the rotating plate 121 is rotated, for example, the original position of the rotating plate 121 may be obtained by a transmission sensor detecting a small hole in the rotating plate 121 and its information may be provided to the analyzer.

The drive part 130 shown in FIG. 4 rotates the rotating plate 121, and the first photodetector 10A and the second photodetector 10B shown in FIG. 4 moves from the outermost position P1 to the innermost position P2 of the rotating plate 121 linearly and in synchronization. With this movement, the first photodetector 10A and the second photodetector 10B moves relative to each DNA chip 1 on the rotator 121 and the irradiation system 11 of the first photodetector 10A emits green irradiation light 25 to the target area 3T of the sample and the irradiation optical system 11 of the second photodetector 10B emits read irradiation light 25 to the target area 3T of the sample.

As the green irradiation light 25 is emitted to the sample target area and the red irradiation light 25 is emitted to the sample target area, fluorescent dye of the target area 3T of the sample emits light. Light emission of the fluorescent dye is received by the photodetecting part 33 of FIG. 1, sent as a signal to the analyzer 50 and the analyzer 50 analyzes the sample based on the fluorescence intensity ratio.

As described above, the plural DNA chips are subjected to scanning of both of the first photodetector 10A and the second photodetector 10B. Rotation of the rotator 121 is continuously performed by the drive part 130. Then, the first photodetector 10A and the second photodetector 10B performs scanning linearly on the rotator 121 by use of the respective actuators 141 and 142.

The first photodetector 10A and the second photodetector 10B shown in FIG. 4 are lighter in weight than the rotator 121 and drive part 130, and it is easy to scan linearly along the radial direction R of the rotator 121. The first photodetector 10A and the second photodetector 10B have a high degree of flexibility in scanning. The measurement object reader 100 is capable of reading samples of plural DNA chips on the rotating plate 121 at high speeds and with low noise. Besides, the rotating plate 121 acts to rotate the DNA chips 1 only and there is no need to move the rotating plate 121 linearly, which allows downsizing and space savings, as compared with the system of moving in X and Y directions of a table with DNA ships 1 placed on.

In a comparative example of the embodiment of the present invention, the optical systems are positionally fixed and one large-sized driving device moves a rotator linearly and rotates the rotator continuously. Contrasted with this example, in the present invention, it is possible to realize reading of a sample as a measurement object at high speeds and with low vibrations. In other words, in the comparative example, as the rotator is continuously rotated while moved linearly with respect to the optical systems, the rotation is apt to vibrate due to rotation and linear movement of the rotator itself.

Further, in another comparative example, light emitted from the irradiation optical system moves in the X direction and Y direction perpendicular to the X direction. With this structure, photodetection of fluorescence is performed at low speeds and there is apt to occur vibration.

In each of the first photodetector 10A and the second photodetector 10B shown in FIG. 4, the irradiation optical system 11 and the reception optical system 12 are completely separated from each other. As the irradiation light 25 is shielded by the tube member 26 and the fluorescence 40 is shielded by the tube member 36, noise such as reflected light or the like from a foreign matter is not input to the core 31L of the second optical fiber 31 and the noise is prevented in the reception optical system 12.

The first photodetector 10A and the second photodetector 10B shown in FIG. 4 conduct detection on the plural DNA chips 1 on the rotator 121 within the same detection range, preferably, in such a manner that the number of rotations of the rotator 121 falls within 25. With this structure, the irradiation optical system 11 irradiates the same sample with light of different wavelengths, and the different wavelengths are used as a basis to surely detect fluorescence of the one sample, thereby making it possible to read properties of the sample with a different fluorescence ratio.

Once the first photodetector 10A and the second photodetector 10B detecting the plural DNA chips 1 on the rotator 121 in a spiral pattern to obtain detected data, the detected data of the plural DNA chips 1 is converted after the data in the spiral pattern is allocated in a matrix pattern. The allocation of the detected data can be performed by averaging of adjacent values or using maximum and minimum values. With this allocation, it is possible to arrange the detected data in accordance with plural samples arranged on the DNA chip 1.

As to the detection sampling speed for the plural DNA chips 1 on the rotator 121 shown in FIG. 4, measurement of samples of DNA chips on the circumference of the rotator 121 is conducted at high speeds and measurement of samples of DNA chips on the inside of the rotator 121 is conducted at low speeds. The speed can be gradually changed depending on the distance along the radial direction from the rotation center of the rotator 121. This change in speeds makes it possible to keep even measurement distance between samples on each DNA chip.

As to the rotation speed of the rotator 121, measurement of samples of DNA chips on the circumference of the rotator 121 is conducted at low speeds and measurement of samples of DNA chips on the inside of the rotator 121 is conducted at high speeds. The speed can be changed gradually. This change in speeds makes it possible to keep even measurement distance between samples on each DNA chip.

In the irradiation optical system 11, the focal point distance of the irradiation light 25 can vary from Z1 to Zn to obtain detected data of samples plural times (n times). In this case, the irradiation optical system 11 is moved along the first optical axis 51, and thereby it is possible to extract optimal data from sample data obtained depending respective focal point distances from the sample target area.

By the way, the present invention is not limited to the above-described embodiments and may be modified in various forms without departing from the scope of the claims of the present invention.

For example, in the above-described example, a sample 3 of the DNA chip 1 shown in FIG. 3 is a DNA segment. However, the sample 3 of the DNA chip 1 may not be DNA segment but RNA segment.

The first photodetector 10A and the second photodetector 10B shown in FIG. 4 can be structured to move linearly by one actuator. The first photodetector 10A and the second photodetector 10B are arranged in opposite direction relative to the center of the rotation center axis 134, and the scan direction of each of the first photodetector 10A and the second photodetector 10B goes along the direction of the diameter of the disk-shaped rotating plate 121. However, this is not for limiting the present invention and the position of each of the first photodetector 10A and the second photodetector 10B relative to the rotating plate 121 can be selected freely.

The number of photodetectors is not limited to two as shown in FIGS. 4 and 5, but may be three or more.

The wavelengths of irradiation light emitted from the irradiation optical system of each photodetector may be limited to green and red wavelengths of this embodiment, but may be selected freely.

Figure 7:
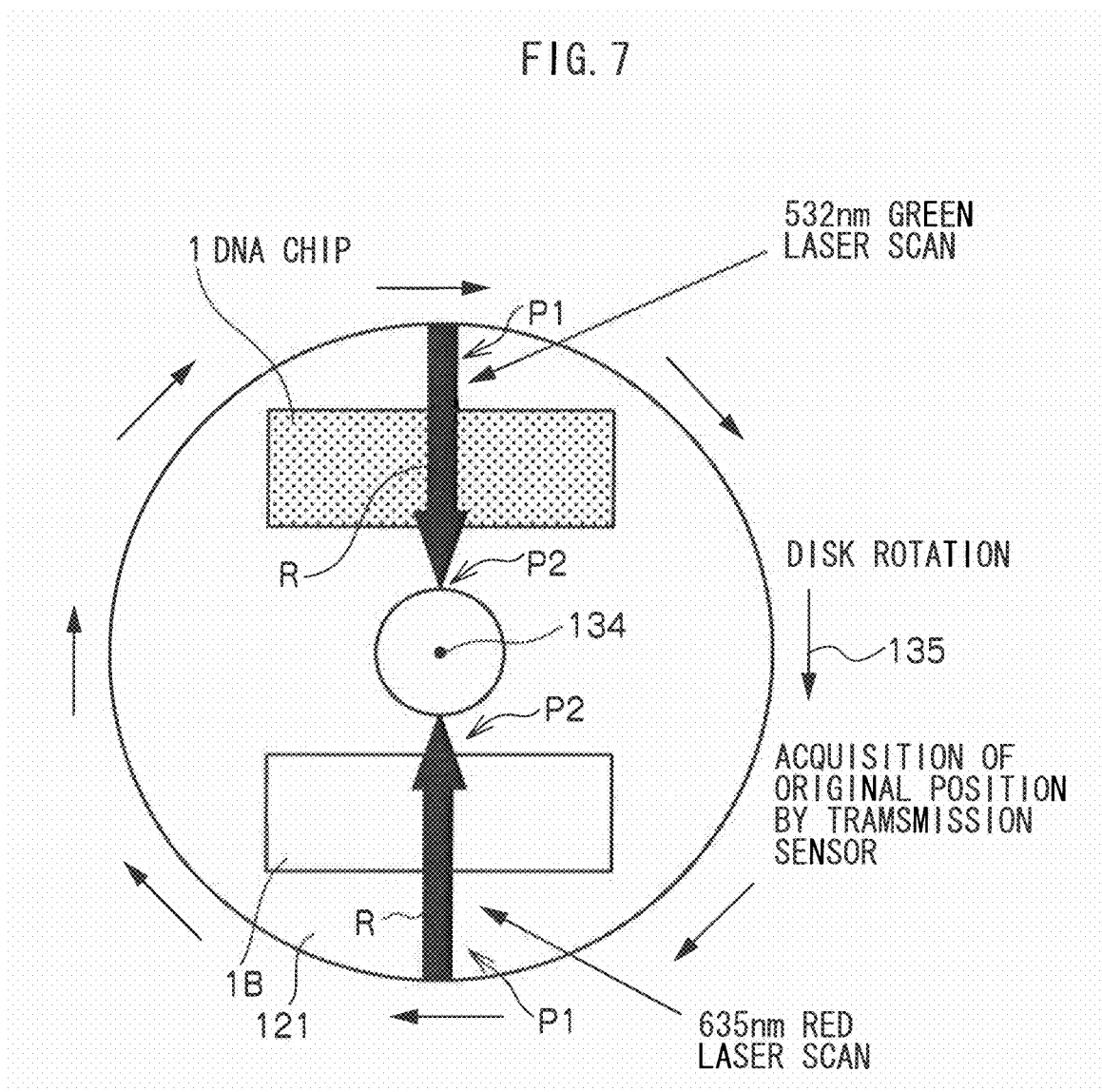
FIG. 7 is a view illustrating another embodiment of the present invention.

In the embodiment of the measurement object reader of the present invention, for example, as shown in FIG. 7, a plurality of chips 1A and 1B of the same kind or different kinds may be fixed detachably on the rotating plate as the rotator (also called "circular disk") to be measured. As these plural chips 1A and 1B are detachable from the rotating plate 121, the preparation methods may be differentiated between them. This structure makes it possible to fix and measure not only same-kind chips 1A and 1B, but also different-kind chips 1A and 1B.

The plural chips 1A and 1B arranged may be a gene expression analysis chip and a genomic analysis chip, and the measurement object reader is able to analyze the simultaneously. This enables simultaneous conduction of gene expression analysis chip and genomic analysis.

Figure 8:
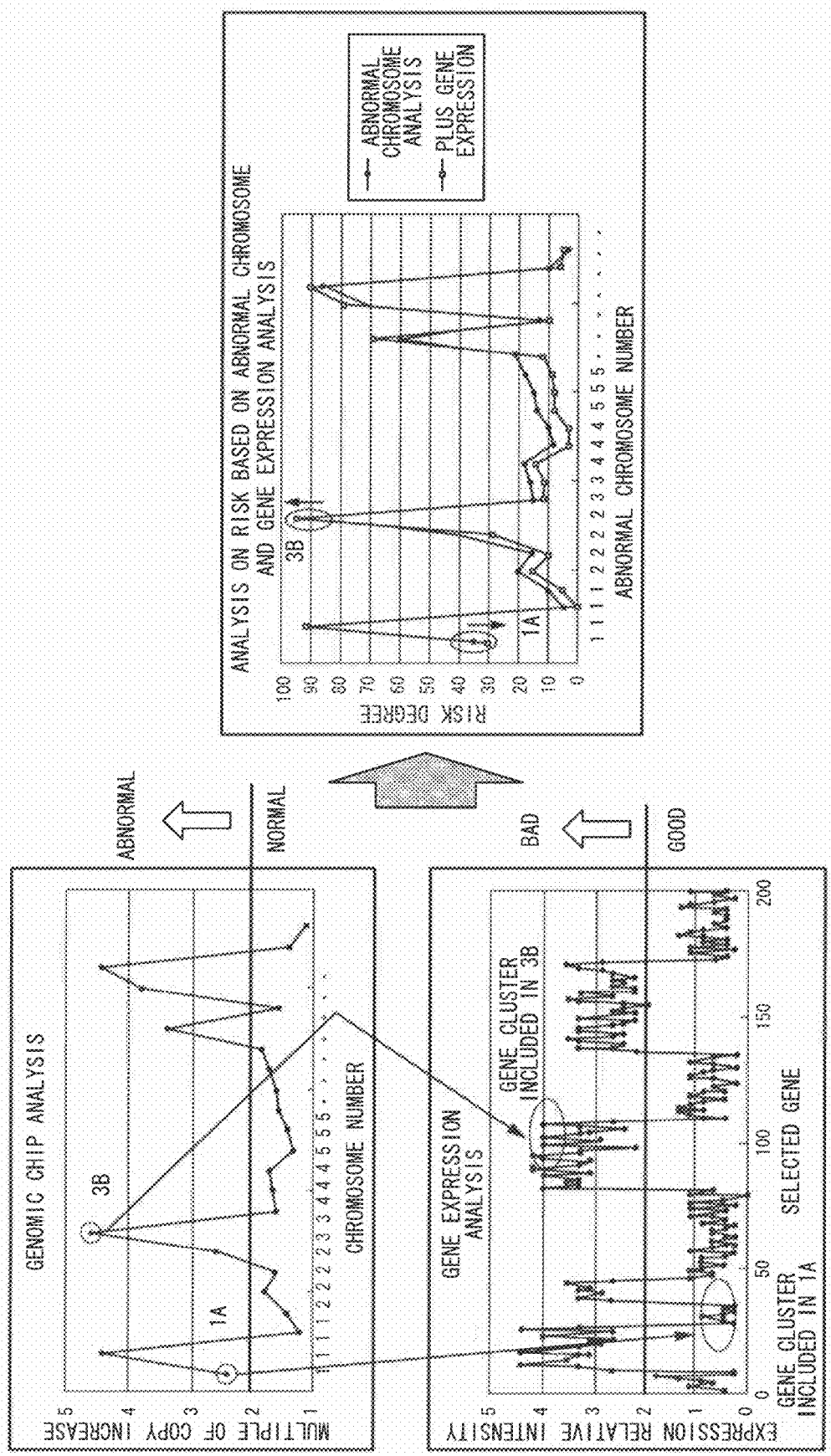
FIG. 8 is a view illustrating another embodiment of the present invention.

The gene expression analysis chip and the genomic analysis chip can be analyzed to form a total analysis result. For example, FIG. 8 shows an analysis result of the gene expression analysis chip and genomic analysis. As the genomic analysis result includes much information and shows variation in data. However, this genomic analysis result is combined with the gene expression analysis thereby to be able to enhance accuracy.

In FIG. 8, the genomic analysis (abnormal chromosome analysis) shows several copy number abnormality in a chromosome which is a part of the chromosome 1, for example. However, gene expression analysis of gene included in this portion shows an excellent result. When these results are judged totally, the degree of risk is smaller than the case of only abnormal chromosome analysis performed. In addition, the chromosome 3B as a part of the chromosome 3, for example, shows clear copy number abnormality. However, gene expression analysis of gene included in this portion shows a bad result. When these results are judged totally, the degree of risk is larger than the case of only abnormal chromosome analysis performed.

In this way, the plural analyses are used as a basis to lead to a total analysis result, thereby allowing examination with high accuracy. Besides, the gene expression analysis chip and the genomic analysis chip are measured and analyzed simultaneously thereby to prevent mixing up of patient samples.

Next description is made about another embodiment of the present invention.

Figure 9A:
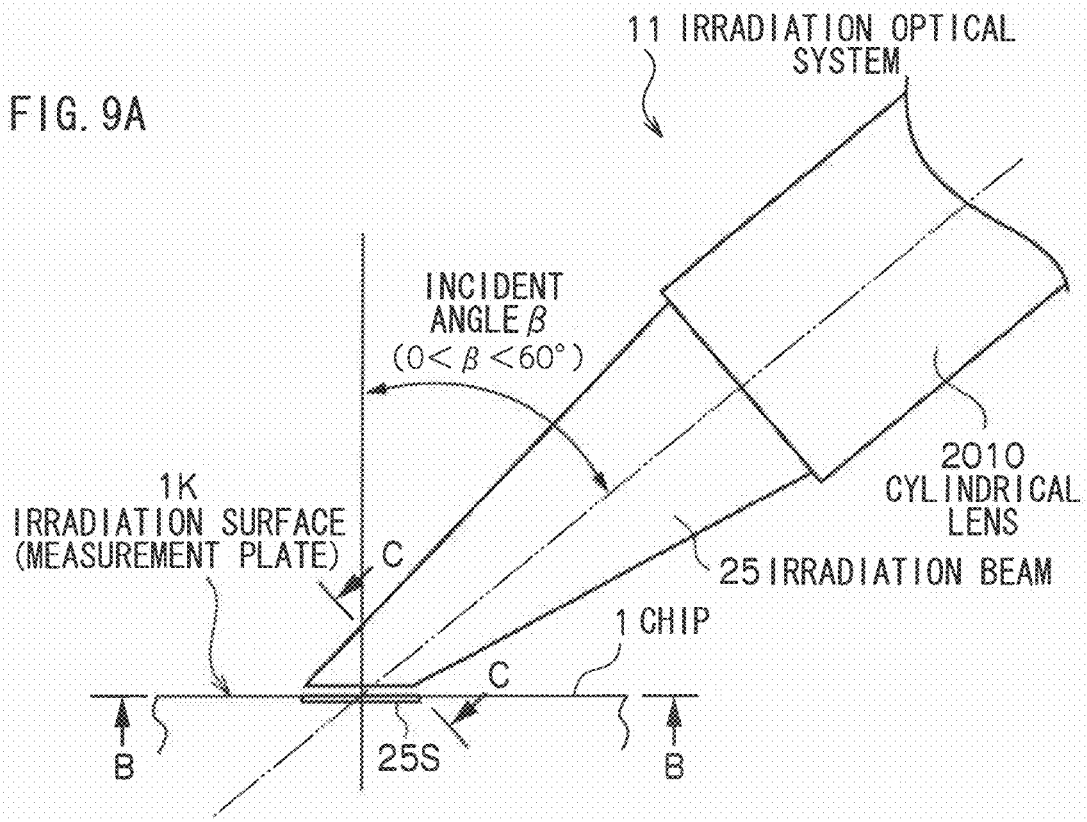
FIGS. 9A to 9C are views illustrating a photodetector according to another embodiment of the present invention.
Figure 9B:
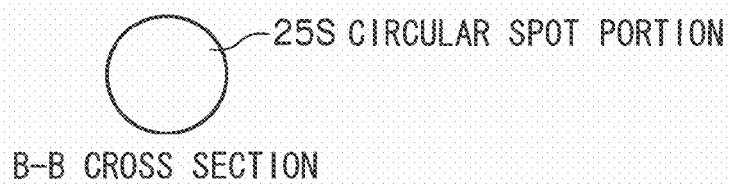
Figure 9C:

FIG. 9A shows the photodetector in which the irradiation light 25 emitted from the irradiation optical system 11 is inclined by the irradiation angle however, a spot area 25S of the DNA chip 1 as a measurement object is formed like a circle. FIG. 9B is a cross sectional view taken along B-B of FIG. 9A, showing the circular spot area 25S. FIG. 9C is a cross sectional view taken along C-C of FIG. 9A, showing the irradiation light 25 in the shape of an ellipse.

The irradiation light 25 shown in FIG. 9A is formed into the ellipse-shaped irradiation light shown in FIG. 9C with use of a cylindrical lens 2010, and the circular spot area as shown in FIG. 9B can be formed on the DNA chip 1. In this case, the irradiation angle of the irradiation light 25 (insert angle α) is 10<α<600. When the circular spot area 25S is thus formed to irradiate the irradiation surface 1K of the DNA chip 1, following advantages are obtained.

Figure 10A:
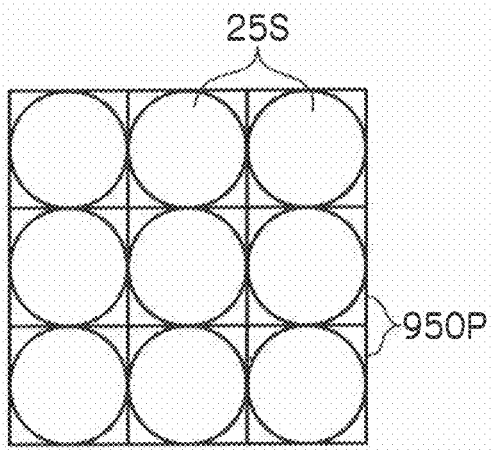
FIGS. 10A and 10B are views for showing circle spot portion and an ellipse-shaped spot portion as a comparative example.
Figure 10B:
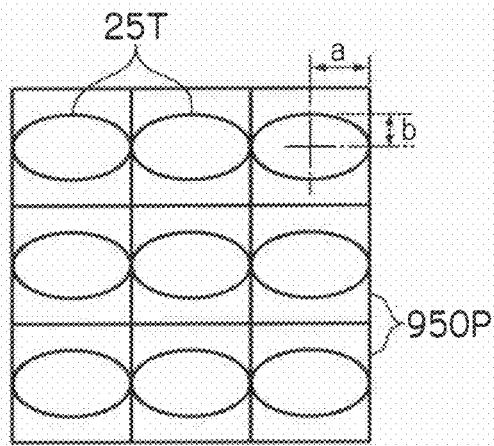

FIG. 10A shows pixels 950P of the photodetecting unit of the reception optical system and circular spot areas 25S scanned in the respective pixels 950P. FIG. 10B shows, as a comparative example, pixels 950P and ellipse-shaped spot areas 25T scanned in the respective pixels 950P.

When comparison is made between FIG. 10A and FIG. 10B, in the one irradiation optical system 11 of FIGS. 9A to 9C, even irradiation to the square pixel 950P in imaging is possible in a circular spot area 25S as compared with the ellipse-shaped spot areas 25T. For example, in FIG. 10A, the circular spot are 25S is expressed by (circle ratio/4) about 79% of the area of the pixel 950P, while in FIG. 10B, the ellipse-shaped spot area 25T is about (b/a×79)% of the area of the pixel 950P and becomes smaller. Here, b denotes a short axis length of the ellipse-shaped spot area 25T and a is a long axis length of the ellipse-shaped spot area 25T.

Preferably, this spot area 25S has a noncircular ratio of 20% or less. This noncircular ratio is a value of a difference between the diameter of the smallest circumcircle and the diameter of the biggest incircle with respect to the typical spot diameter, which is expressed in percent figures, and shows distortion from the perfect circle. This definition also applies to the ellipse-shaped spot area.

In order to show a value in pixel accurately, the spot outside of the pixel is not preferable and the diameter of the smallest circumcircle of the spot area is preferably equal to or less than one side of a square pixel. Then, the shape of the spot area appropriate to the widest irradiation in the pixel is a perfect circle and the irradiation area becomes about 79% of the pixel. When the non circular ratio becomes 20%, the irradiation area becomes a smallest value of about 50%. Therefore, if the noncircular ration exceeds 20%, more than a half of values in pixel can not be reflected undesirably.

FIG. 11 shows the plural photodetectors 10A and 10B arranged on the rotating plate 121, the photodetectors 10A and 10B move linearly toward the center of the rotating plate 121 or in its opposite direction R by the respective actuators 141. Besides, the photodetectors 10A and 10B are able togo and return toward the center of the rotating plate 121 or in its opposite direction R thereby to detect the DNA chips. The rotating plate 121 is continuously rotated as drive by the motor 130, for example, along the arrows 135. With this movement, the plural photodetectors 10A and 10B are able to conduct plural times of detection on the DNA chips as measurement objects with high efficiency, and complement of detection results are performed to enhance the reliability.

Thus, when the photodetectors 10A and 10B go and return toward the center of the rotating plate 121 or in its opposite direction R, the speed of movement of each of the photodetectors 10A and 10B can be changed between the onward path R-1 and return path R-2. For example, the DNA chip 1 is moved at high speeds in the onward path R-1 to make rough detections and the DNA chip 1 is moved at low speeds in the return R-2 thereby to allow minute detections. The result in the onward path R-1 includes a small amount of data, the data processing is facilitated, and only a necessary part of the processing result is extracted to be used with reference to a result in the return path R-2 thereby allow data processing with high efficiency.

Further, the speeds of the onward path and the return path can be changed during movement of the photodetectors 10A and 10B. For example, on the basis of the result of the onward path R-1, each photodetector moves at low speeds only in a necessary part of the return path R-2. In this movement, determination of the necessary part can be made manually after finish of the onward path R-1, or can be made automatically by a controller. This makes it possible to extract only necessary data in details, thereby allowing highly-efficient measurement and data processing.

For example, in the measurement object reader shown in FIG. 4, while the rotating plate 121 rotates, the photodetectors 10A and 10B make measurements of some orbits and not of the other orbits. In an orbit of which measurement is not performed, measured data of chips is transferred to the analyzer, which can perform analysis on the measured data until it comes to a next orbit of which measurement is not to be performed.

Figure 12:
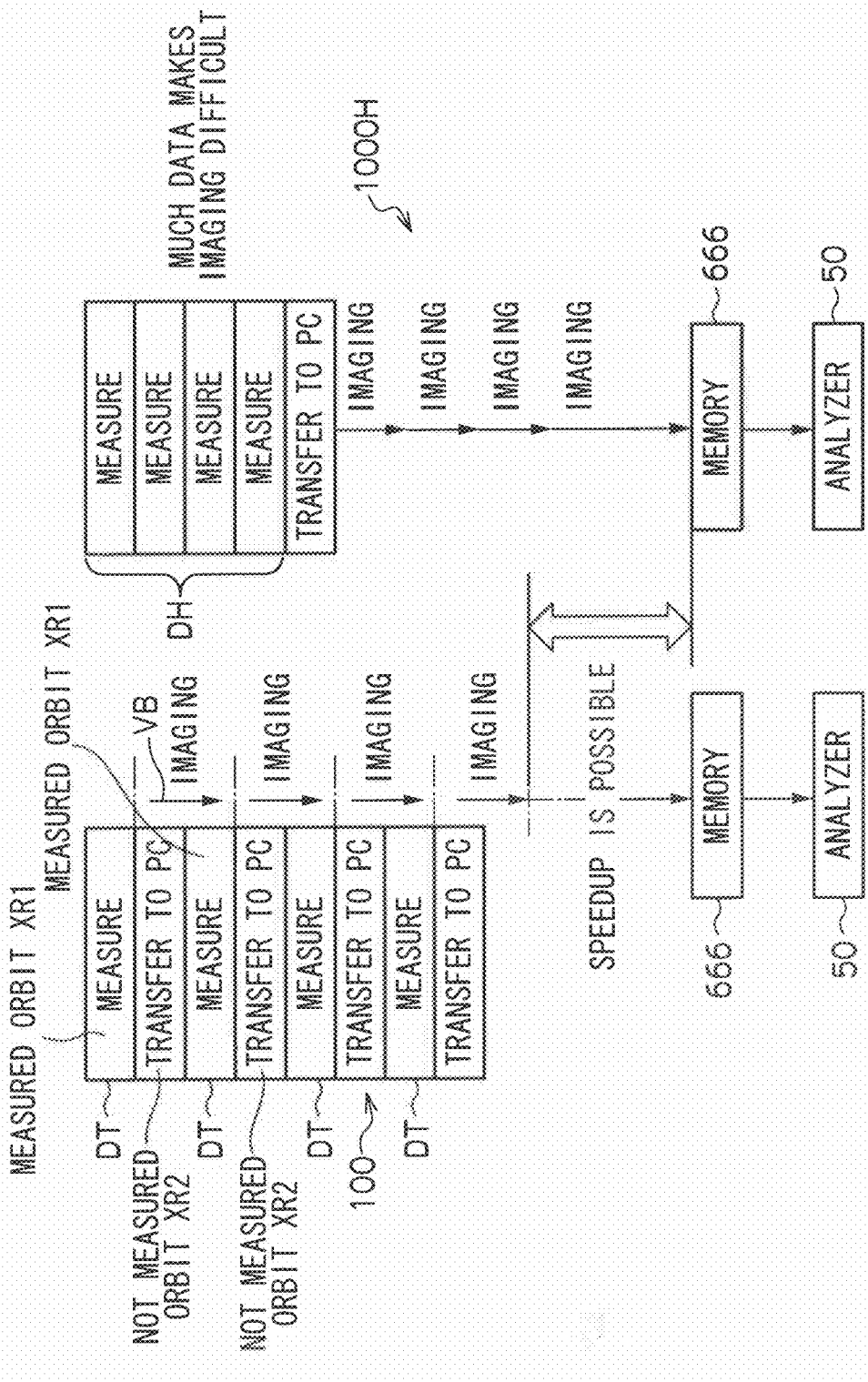
FIG. 12 is a view showing an example of transferring measured data of DNA chip and its comparative example.

FIG. 12 illustrates an example of processing of measured data when the measurement object reader conducts measurements. In FIG. 12, for example, the photodetectors 10A and 10B shown in FIG. 11 determine orbits to be measured XR1 and orbits not to be measured XR2. For the orbits to be measured XR1, measured data DT of one orbit is stored in the memory 666, while in an orbit not to be measured XR2, the data is transferred from the memory 666 to the analyzer 50 and analyzing of the measured data DT continues until the next orbit not to be measured. As a comparative example of the measurement object reader 100, FIG. 12 also shows processing of measured data by another measurement object reader 1000H.

In the measurement object reader 1000H of a comparative example in FIG. 12, measured data DH are all stored in the memory 666. However, as the content of the measured data DH increased in proportion to the square of a pixel resolution in imaging, the resolution in imaging of the measurement object reader 1000H is restricted by the capacity of the memory 666. On the other hand, in the measurement object reader 100, while the rotating plate 121 shown in FIG. 4 rotates, the photodetectors 10A and 10B has orbits to be measured XR1 and orbits not to be measured XR2. The measured data DT of about one orbit is stored in the memory 666, while in an orbit not to be measured XR2, the data is transferred to the analyzer 50. Therefore, the capacity of the memory 666 does not have to be large and the resolution is not restricted by the capacity of the memory 666 even in obtaining high-resolution image data.

Further, in the measurement object reader 100 as the orbits not to be measure XR2 are provided, the time required for completion of all measurements becomes about twice. However, the time other than the time for transfer in the orbits not to be measured can be utilized for imaging processing, and particularly, when the total time for imaging is longer than the total time for measurement, the processing can be performed with high efficiency thereby realizing speedups.

Further, in the example, the operation performed in the orbits not to be measured may be performed in the orbits to be measured XR1. For example, in the orbits to be measured XR1, around the time when a DNA chip 1 is detected as a measurement object, storing into the memory 666 is performed, and the time when detection is not performed is only utilized to transfer the data from the memory 666 to the analyzer 50 like in the orbits not to be measured XR2 then to conduct imaging processing thereby obtaining the same effects. The number of DNA chips 1 to be analyzed by the analyzer 50 in FIG. 12 may be one or more.

Figure 13:
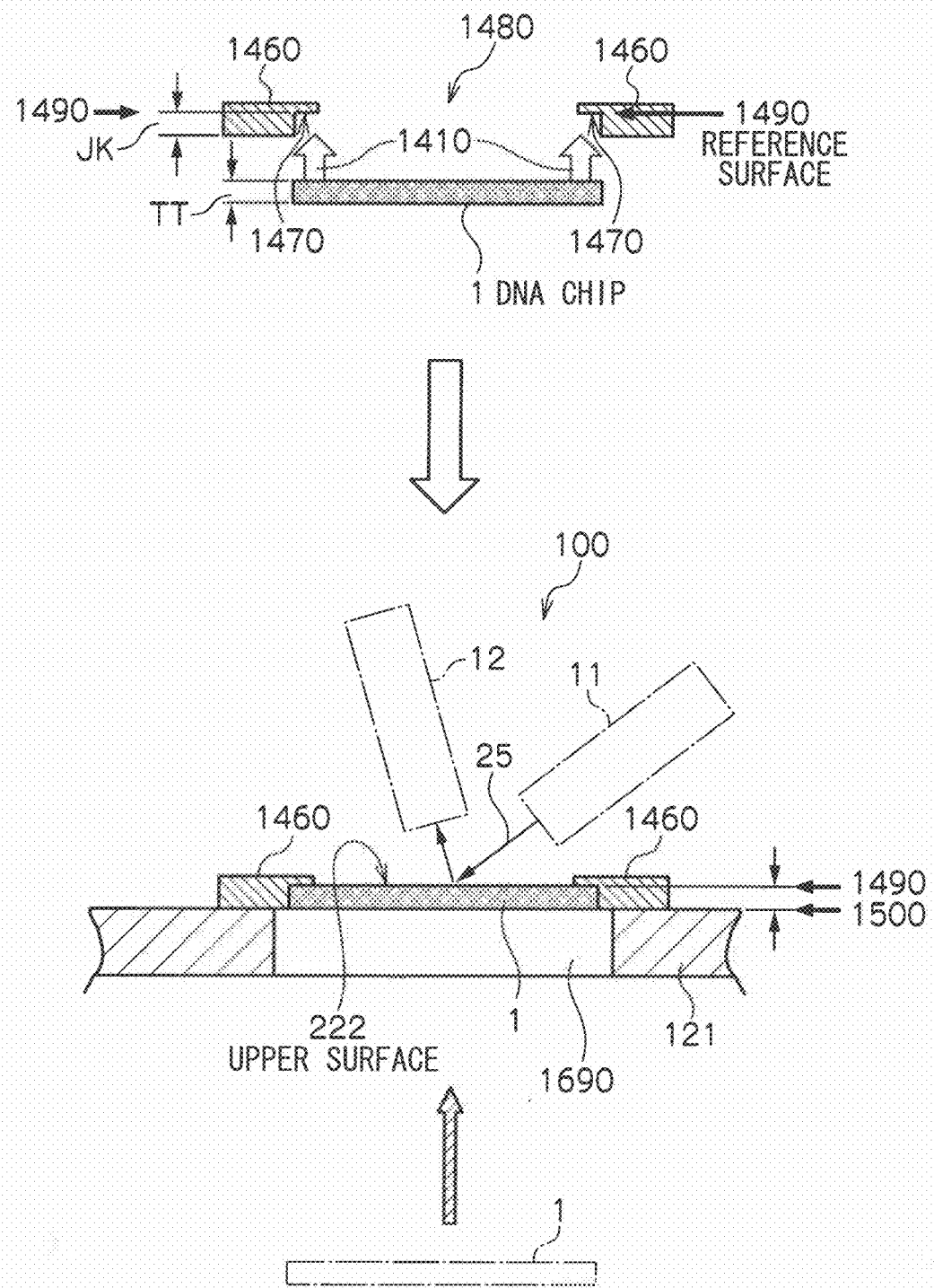
FIG. 13 is a view illustrating a member for setting a reference surface of the DNA chip.

FIG. 13 shows when the irradiation optical system 11 of the measurement object reader 100 obtains correct focus of light on the DNA chip 1, an upper surface 222 of the chip 1 is used as a reference. In FIG. 13, a reference surface setting member 1460 is a member for holding the DNA chip 1 by inserting the DNA chip 1 therein, and has a step portion 1470.

The step portion has a rectangular opening 1480 formed therein. The rotating plate 121 preferably has an opening 1690 formed therein. For example, the DNA chip 1 is inserted through the opening 1690 of the rotating plate 121 and into the step portion 1470, and the upper surface 222 of the DNA chip 1 is pushed against the reference surface 1490. With this structure, if the thickness TT of each DNA chip 1 has an elevation change, the upper surface 222 of the DNA chip 1 is positionally fixed relative to the mount surface 1500 of the rotating plate 121. Accordingly, when the irradiation optical system 11 of the measurement object reader 100 obtains correct focus of light on the DNA chip 1, irradiation light 25 is emitted onto the upper surface 222 of the chip 1 used as reference, thereby enhancing measurement accuracy.

FIG. 16 shows arrangement of samples in a matrix in such a manner that they are arranged parallel to or vertical to the radial direction of the rotator. In a standard DNA chip, the plane where the samples 3 are arranged is shaped like a square or rectangle. The plane is often a rectangle having 1 inch×3 inch, sometimes sharp edges of the rectangle are rounded, however, the plane shape is approximately a square or rectangle as a whole. Such a standard DNA chip has a plurality of samples which are arranged in an orderly manner so that it can be seen what sample are positioned on the DNA chip 1. As shown in FIG. 16, they are arranged in parallel with or vertical to one side of the DNA chip 1. The samples 3 are often arranged in a matrix as shown in the DNA chip 1A, however, they may be arranged offset as shown in the DNA chip 1B. The measurement object reader 100 is structured to measure the DNA chip 1, detachable from the rotating plate (circular disk) 121, on which rows and columns of the samples 3 is arranged approximately in parallel with or perpendicular to the radial direction R of the rotating plate 121. The measurement object reader 100 is structured to measure many and standard DNA chips that exist generally including a DNA chip having a circle-disk shaped plane on which the samples are arranged, a special chip on which the samples are arranged along the circumference or, for example, spirally.

The present invention is applicable to various fields including a field that needs test, mapping and analysis on biological macromolecule such as saccharide, amino acid and protein, immune system, gene, engineering, agricultural science such as food, agrotechny, fish processing or the like, pharmaceuticals, medical science such as gene, epidemic, immunity, health care, hygienics or the like, and science such as chemistry, biology or the like.

The invention claimed is:

1. A photodetector for detecting light emitted from a sample on a substrate as a measurement object, the photodetector comprising:
   an irradiation optical device comprising a first optical waveguide guiding irradiation light, and a first lens for receiving and gathering the irradiation light from the first optical waveguide and irradiating the sample as the measurement object; and
   a reception optical device comprising a second lens for gathering light emitted from the sample and a second optical waveguide for receiving the light at an input-side end surface from the second lens and guiding the light to a measuring unit; and
   an irradiation light spot converting portion which converts a spot shape of the irradiation light output from the irradiation optical device in such a manner that the spot shape becomes circular on an installation plane on which the measurement object is placed, wherein,
   the irradiation optical device and the reception optical device are separate light guiding paths, each optical device having an optical axis oriented at a different angle with respect to an axis perpendicular to the installation plane on which the measurement object is placed, the optical axis of the reception optical device has the angle other than 0 degrees with respect to the axis perpendicular to the installation plane,
   the first optical axis of the irradiation optical device forms an angle, except for 0 degree, with respect to a normal line of the installation plane on which the measurement object is placed, and
   the reception optical device is of a confocal optical device in which a focal point on the sample is identical to a focal point at the input-side end surface of the second optical waveguide of the reception optical device.

2. The photodetector of claim 1, wherein, in a plane perpendicular to the installation plane on which the measurement object is placed, a first plane including a first optical axis of the irradiation optical device and a second plane including a second optical axis of the reception optical device are not coplanar.

3. The photodetector of claim 1, wherein a center of a first optical axis of the irradiation optical device and a center of a second optical axis of the reception optical device are inclined at respective angles relative to the axis perpendicular to an installation plane on which the measurement object is placed.

4. The photodetector of claim 3, wherein the axis perpendicular to the installation plane on which the measurement object is placed and the center of the first optical axis of the irradiation optical device form an angle ranging from 10 degrees to 60 degrees, inclusive.

5. The photodetector of claim 3, wherein the axis perpendicular to the installation plane on which the measurement object is placed and the center of the second optical axis of the reception optical device form an angle ranging from 10 degrees to 80 degrees, inclusive.

6. The photodetector of claim 5, wherein a size of a light gathering surface of the irradiation optical device is equal to or less than one fifth of a size of a spot area for measurement.

7. The photodetector of claim 6, wherein a GRIN (Gradient Index) lens is arranged on an input-side end surface of the irradiation light in the first waveguide of the irradiation optical device.

8. The photodetector of claim 7, wherein a numerical aperture of the second lens of the reception optical device is larger than a numerical aperture of the second optical waveguide.

9. The photodetector of claim 8, wherein a mode field diameter (MFD) of the reception optical device is adjustable.

10. The photodetector of claim 1, wherein a noncircular ratio of the spot shape is equal to or less than 20%.

11. The photodetector of claim 1, wherein a cylindrical lens is used to form a circular spot.

12. A measurement object reader having a photodetector for detecting light emitted from a sample on a substrate as a measurement object, the measurement object reader comprising:
an irradiation optical device comprising a first optical waveguide for guiding irradiation light, and a first lens for receiving and gathering the irradiation light from the first optical waveguide and irradiating the sample as the measurement object;
a reception optical device comprising a second lens for gathering light emitted from the sample and a second optical waveguide for receiving the light at an input-side end surface from the second lens and guiding the light to a measuring unit;
an irradiation light spot converting portion which converts a spot shape of the irradiation light output from the irradiation optical device in such a manner that the spot shape becomes circular on an installation plane on which the measurement object is placed, wherein,
the reception optical device is a light guiding path separate from a light guiding path of the irradiation optical device, each optical device having an optical axis oriented at a different angle with respect to an axis perpendicular to the installation plane on which the measurement object is placed, the optical axis of the reception optical device has the angle other than 0 degrees with respect to the axis perpendicular to the installation plane,
the first optical axis of the irradiation optical device forms an angle, except for 0 degree, with respect to a normal line of the installation plane on which the measurement object is placed, and
the reception optical device is of a confocal optical device in which a focal point on the sample is identical to a focal point at the input-side end surface of the second optical waveguide of the reception optical device;
a measurement object rotating part having a rotator and rotating the rotator with the sample on the substrate as the measurement object placed thereon;
the photodetector for emitting the irradiation light onto the sample as the measurement object on the rotator thereby to read fluorescence emitted from the sample; and
a mechanism for linearly moving the photodetector or an irradiation spot toward a center of the rotator or in an opposite direction thereof.

13. The measurement object reader of claim 12, wherein the photodetector comprises a plurality of photodetectors.

14. The measurement object reader of claim 13, wherein,
the plural photodetectors are arranged in opposite directions about a rotational center of the measurement object rotating part, and
the plural photodetectors use light of different wavelengths.

15. The measurement object reader of claim 14, wherein, when each of the photodetectors detects the measurement object in a spiral pattern while the rotator is rotated thereby to obtain detection data of the measurement object, the detection data of the measurement object is converted from the spiral pattern into a row-and-column matrix pattern.

16. The measurement object reader of claim 15, wherein,
there are an orbit at which each of the photodetectors conduct measurement and an orbit at which the photodetector does not conduct measurement while the rotator rotates,
in the orbit at which the photodetector does not conduct measurement, measured data of a chip is transferred from a memory to an analyzer, and
the measured data is analyzed by a next orbit at which the photodetector does not conduct measurement.

17. The measurement object reader of claim 16, wherein chips to be analyzed are single or plural.

18. The measurement object reader of claim 14, wherein,
a detection sampling speed of the measurement object is increased in measurement of the measurement object at an outer orbit portion of the rotator and decreased in measurement of the measurement object at an inner orbit portion of the rotator, and
the speed is changed gradually.

19. The measurement object reader of claim 14, wherein,
a rotational speed of the rotor is decreased in measurement of the measurement object at an outer orbit portion of the rotator and increased in measurement of the measurement object at an inner orbit portion of the rotator, and
the speed is changed gradually.

20. The measurement object reader of claim 14, wherein,
the plural photodetectors moves linearly toward the center of the rotator or in an opposite direction thereof, and
the plural photodetectors reciprocate toward the center of the rotator or in the opposite direction thereof thereby to perform detection.

21. The measurement object reader of claim 20, wherein in reciprocating, the photodetectors move at different speeds between an initial path and a return path.

22. The measurement object reader of claim 12, wherein the irradiation optical device and the reception optical device move together while maintaining their relative positions of the confocal optical system device.

23. The measurement object reader of claim 12, wherein,
the photodetector comprises a plurality of photodetectors, and
when each of the photodetectors detects the measurement object in a spiral pattern while the rotator is rotated thereby to obtain detection data of the measurement object, the detection data of the measurement object is converted from the spiral pattern into a row-and-column matrix pattern.

24. The measurement object reader of claim 12, wherein,
a detection sampling speed of the measurement object is increased in measurement of the measurement object at an outer orbit portion of the rotator and decreased in measurement of the measurement object at an inner orbit portion of the rotator, and
the speed is changed gradually.

25. The measurement object reader of claim 12, wherein,
a rotational speed of the rotor is decreased in measurement of the measurement object at an outer orbit portion of the rotator and increased in measurement of the measurement object at an inner orbit portion of the rotator, and
the speed is changed gradually.

26. The measurement object reader of claim 12, wherein detection data of the sample is obtained plural times by changing a focal point distance of the light in the irradiation optical device.

27. The measurement object reader of claim 12, wherein, the rotator is a circular disk, and
a plurality of chips of similar or different kinds is detachably fixed onto the round disk thereby to enable measurement of the plurality of chips.

28. The measurement object reader of claim 27, wherein the plurality of chips is analyzed simultaneously.

29. The measurement object reader of claim 28, wherein analysis results of the plurality of chips are analyzed comprehensively.

30. The measurement object reader of claim 29, wherein some of the plurality of chips are different in pretreatment method.

31. The measurement object reader of claim 29, wherein the plurality of chips includes a gene expression analysis chip and a genomic analysis chip.

32. The measurement object reader of claim 27, wherein as the irradiation optical device gathers a focal point of the light on each of the chips, an upper surface of the chip is used as a reference.

33. The measurement object reader of claim 27, wherein each of the chips has samples of which rows and columns arranged in parallel with or vertical to a radial direction of the rotator.

34. The measurement object reader of claim 33, wherein, in each of the chips, a plane where the samples are placed is shaped like a rectangle or a square.

* * * * *